United States Patent
Price

(10) Patent No.: US 9,693,845 B2
(45) Date of Patent: Jul. 4, 2017

(54) METHOD AND SYSTEM FOR MEASUREMENT OF CURING ENERGY DELIVERED DURING SIMULATED DENTAL RESTORATIONS

(75) Inventor: Richard Bengt Price, Halifax (CA)

(73) Assignee: BlueLight Analytics, Inc., Halifax (CA)

( * ) Notice: Subject to any disclaimer, the term of this patent is extended or adjusted under 35 U.S.C. 154(b) by 583 days.

(21) Appl. No.: 13/260,525

(22) PCT Filed: Apr. 8, 2010

(86) PCT No.: PCT/CA2010/000499
§ 371 (c)(1),
(2), (4) Date: Sep. 26, 2011

(87) PCT Pub. No.: WO2010/115274
PCT Pub. Date: Oct. 14, 2010

(65) Prior Publication Data
US 2012/0026307 A1    Feb. 2, 2012

Related U.S. Application Data

(60) Provisional application No. 61/168,039, filed on Apr. 9, 2009.

(51) Int. Cl.
| | |
|---|---|
| *G01N 21/17* | (2006.01) |
| *A61C 19/04* | (2006.01) |
| *G09B 23/28* | (2006.01) |
| *G09B 9/00* | (2006.01) |
| *A61C 13/15* | (2006.01) |
| *G06Q 30/02* | (2012.01) |

(52) U.S. Cl.
CPC ........... *A61C 19/004* (2013.01); *A61C 19/04* (2013.01); *G06Q 30/02* (2013.01); *G09B 23/283* (2013.01);

(Continued)

(58) Field of Classification Search
None
See application file for complete search history.

(56) References Cited

U.S. PATENT DOCUMENTS 4,102,047 A * 7/1978 Walker .......................... 434/263
4,435,163 A * 3/1984 Schmitt et al. ............... 434/263

(Continued)

FOREIGN PATENT DOCUMENTS

| FR | 2909276 A1 | 6/2008 |
|---|---|---|
| JP | H08-509884 A | 10/1996 |

(Continued)

OTHER PUBLICATIONS

A C Shortall, E. Harrington, H.B. Patel, P.J. Lumley, "A pilot investigation of operator variability during intra-oral light curing," British Dental Journal 2002, vol. 193, No. 5, pp. 276-280, Sep. 14, 2002.

(Continued)

*Primary Examiner* — Anner Holder
*Assistant Examiner* — William Adrovel
(74) *Attorney, Agent, or Firm* — Clark & Elbing LLP

(57) ABSTRACT

A system and method for real-time measurement of curing energy delivered to a simulated dental restoration from a source of curing energy. The system comprises a detector and a display. The detector measures at a location within the simulated dental restoration the amount of curing energy delivered by the curing energy source. The display displays the measured amount of curing energy in real-time. The system also comprises a temperature detector to measure temperature changes in the oral tissues during curing (teeth and gums). The system also comprises a video camera to record the operator's curing technique.

18 Claims, 23 Drawing Sheets

(52) U.S. Cl.
CPC ..... *G01N 21/17* (2013.01); *G01N 2291/0251* (2013.01); *G09B 9/00* (2013.01)

(56) References Cited

U.S. PATENT DOCUMENTS

| | | | |
|---|---|---|---|
| 5,125,842 A | 6/1992 | Hiltunen | |
| 5,536,245 A | 7/1996 | Dahlbeck | |
| 5,688,118 A | 11/1997 | Hayka et al. | |
| 5,738,678 A | 4/1998 | Patel | |
| 5,759,030 A * | 6/1998 | Jung et al. | 433/29 |
| 6,089,740 A * | 7/2000 | Forehand et al. | 362/573 |
| 6,254,389 B1 | 7/2001 | Seghatol | |
| 6,850,222 B1 | 2/2005 | Rosenberg | |
| 7,106,958 B2 | 9/2006 | Kerschbaumer et al. | |
| 7,140,770 B2 | 11/2006 | Westerlund | |
| 7,175,436 B2 | 2/2007 | Friedman | |
| 7,530,812 B2 | 5/2009 | Chyz | |
| 7,537,455 B2 * | 5/2009 | Cope | 434/263 |
| 8,189,189 B1 * | 5/2012 | Herendeen et al. | 356/300 |
| 2002/0119432 A1 * | 8/2002 | Ranta et al. | 434/263 |
| 2002/0192627 A1 * | 12/2002 | Lee et al. | 434/263 |
| 2004/0095507 A1 | 5/2004 | Bishop et al. | |
| 2005/0244975 A1 * | 11/2005 | Rakow et al. | 436/85 |
| 2006/0008762 A1 * | 1/2006 | Friedman | 433/27 |
| 2006/0044555 A1 * | 3/2006 | Wang et al. | 356/301 |
| 2006/0285323 A1 * | 12/2006 | Fowler | G01J 3/10 362/230 |
| 2007/0178429 A1 | 8/2007 | Bell | |
| 2007/0259309 A1 * | 11/2007 | West et al. | 433/29 |
| 2008/0176198 A1 | 7/2008 | Ansari et al. | |
| 2008/0305459 A1 * | 12/2008 | Li et al. | 433/226 |
| 2009/0035739 A1 | 2/2009 | Alemzadeh | |
| 2009/0114844 A1 | 5/2009 | Plank et al. | |
| 2010/0003657 A1 * | 1/2010 | Shibui et al. | 434/267 |
| 2010/0140450 A1 | 6/2010 | Duret et al. | |
| 2011/0136090 A1 * | 6/2011 | Kazemi | 434/263 |
| 2011/0275900 A1 * | 11/2011 | Gilhuly et al. | 600/162 |

FOREIGN PATENT DOCUMENTS

| | | |
|---|---|---|
| JP | H11-503354 A | 3/1999 |
| JP | H11-137574 A | 5/1999 |
| JP | 2005080759 A2 | 3/2005 |
| JP | 2010-511459 A | 4/2010 |
| WO | WO-94/26203 A1 | 11/1994 |
| WO | 2004/019271 A2 | 3/2004 |
| WO | WO-2008/023464 A1 | 2/2008 |

OTHER PUBLICATIONS

International Search Report and Written Opinion mailed Jun. 30, 2010 for PCT/CA2010/000499, filed Apr. 8, 2010, titled Method and System for Measurement of Curing Energy Delivered During Simulated Dental Restorations.
BlueLight analytics inc., "MARC patient simulator version 3.0," (2012) (9 pages).
BlueLight analytics inc., "MARC devices used in six studies to be presented at the IADR 2013 in Seattle" <http://curingresin.com/2013/03/marc-devices-used-in-five-abstracts-at-the-iadr-2013-in-seattle/2911>, retrieved on Feb. 22, 2014 (3 pages).
Christensen, "Save time, effort, and money with fast, new LED curing lights," Clinicians Report 3(10) (2010) (3 pages).
Daily Business Buzz, "NS: BlueLight analytics inc. 'recruited' by U.S. Military dental practice," <http://www.ns.dailybusinessbuzz.ca/Provincial-News/2014-01-16/article-3578972/NS%3A-BlueLight-Analytics-Inc.-recruited-by-U.S.-Military-dental-practice/1>, retrieved on Feb. 22, 2014 (2 pages).
Felix et al., "Effect of reduced exposure times on the microhardness of 10 resin composites cured by high-power LED and QTH curing lights," J Can Dent Assoc. 72(2):147a-f (2006).
Harrison, "Study finds dentists sloppy with curing lights," <http://www.drbicuspid.com/index.aspx?sec=log&URL=http%3a%2f%2fwww.drbicuspid.com%2findex.asp%3fsec%3dser%26sub%3ddef%26pag%3ddis%26ItemID%3d304626>, retrieved on May 25, 2010 (2 pages).
Henry, "On the MARC: an amazing device I tried in Chicago," <http://www.dentistryiq.com/articles/2011/03/on-the-marc-an-amazing-device-i-tried-in-chicago.html> retrieved on Mar. 22, 2011 (1 page).
Inside Dentistry, "Year in review," 8(12) (2012) (11 pages).
Kopperud et al., "Longevity of posterior dental restorations and reasons for failure," Eur J Oral Sci. 120:539-48 (2012).
Price et al., "Effect of delivering light in specific narrow bandwiths from 394 to 515nm on the micro-hardness of resin composites," Dent Mater. 25(7):899-908 (2009).
Price et al., "Effect of distance on irradiance and beam homogeneity from 4 light-emitting diode curing units," J Can Dent Assoc. 77:b9 1-10 (2011).
Price et al., "Factors affecting the energy delivered to simulated class I and class V preparations," J Can Dent Assoc. 76:a94 1-9 (2010).
Price et al., "Knoop microhardness mapping used to compare the efficacy of LED, QTH and PAC curing lights," Oper Dent. 35(1):58-68 (2010).
Price, "Guest editorial: symposium on light sources in dentistry," Den Mater. 29(2):137-8 (2013).
Price, "Light energy matters," J Can Dent Assoc. 76:a63 (2010).
Price et al., "Quantifying light energy delivered to a class I restoration," J Can Dent Assoc. 76:a23 (2010).
Price et al., "The effectiveness of using a patient simulator to teach light-curing skills," J Am Dent Assoc. 145(1):32-43 (2014).
Roberts et al., "Accuracy of LED and halogen radiometers using different light sources," J Esthet Restor Dent. 18(4):214-22 (2006).
Rueggeberg, "State-of-the-art: dental photocuring—a review," Dent Mater. 27:39-52 (2011).
Santini et al., "General dental practitioners' knowledge of polymerisation of resin-based composite restorations and light curing unit technology," Br Dent J. 21 1(6):E13 1-5 (2011).
Seth et al., "Effect of instruction on dental students' ability to light-cure a simulated restoration," J Can Dent Assoc. 78:c123 1-8 (2012).
Strassler, "Successful light curing—not as easy as it looks," <http://www.oralhealthgroup.com/news/successful-light-curing-not-as-easy-as-it-looks-howard-e-strassler-dmd/1002445470/?&er=NA>, retrieved on Feb. 21, 2014 (6 pages).
Watt, "Let there be light!" Dent Mater. 29(6):603-4 (2013).
"MARC patient simulator (PS) dental curing light energy management system (brand name or equal)," <https://www.fbo.gov/index?s=opportunity&mode=form&id=40c0f136c2e951e47389ea0b1e561f5c&tab=core&_cview=1>, retrieved on Feb. 22, 2014 (3 pages).
Extended European Search Report for European Patent Application No. 10761149.3, dated Dec. 19, 2013 (6 pages).
Office Action for Chinese Patent Application No. 201080021771.9, dated Sep. 12, 2013 (23 pages).
Office Action for Japanese Patent Application No. 2012-503838, mailed Aug. 12, 2013 (11 pages).
Federlin, et al., "Improving light-curing instruction in dental school," J Dent Educ. 77(6):764-72 (2013).
Strassler et al., "Understanding light curing, part 2," ADA. Jun. 2014 (11 pages).
American Dental Association, "Product Forum highlights how to improve curing light effectiveness," ADA Professional Product Review. 9(4):26-9 (2014).
English translation of Second Office Action for Chinese Patent Application No. 201080021771.9, dated Jun. 18, 2014.
American Dental Association, Effective Use of Dental Curing Lights: a Guide for the Dental Practitioner, ADA Professional Product Review. 8:2-12 (2013).
American Dental Association, "Jun. 2005 Survey of Dental Services," ADA. Aug. 2007. (181 pages).
National Institute of Dental and Craniofacial Research, "Strategic Plan, 2009-2013," Department of Health and Human Services U S A. published: May 2009. (62 pages).

(56) References Cited

OTHER PUBLICATIONS

Strassler et al., "Understanding light curing, part 1," ADA. May 2014 (11 pages).
Ultradent Company Letter of 2010 from Dan Fischer.
Rueggeberg et al., "Efficacy of a training device for increasing curing energy delivery," Poster No. 4076 (2010).
Harun et al., "The effect of interincisal opening, cavity location and operator experience on the energy delivered by a light-curing unit to a simulated dental restoration," Primary Dental Journal. 3(2):26-31 (2014).
Shortall et al., "Initial fracture resistence and curing temperature rise of ten contemporary resin-based composites with increasing radiant exposure," J Dentistry. 41:455-63 (2013).
Mutluay et al., "Effect of using proper light-curing techniques on energy delivered to a Class 1 restoration," Quintessence International. 45(7):549-56 (2014).
Stephanie Porter, "The light is right—thanks to Bluelight Analytics, your filings and crowns could last longer," Atlantic Business Magazine. p. 111.
Al Shaafi, "Effects of different infection control methods on the intensity output of LED light-curing units," King Saudi Journal of Dental Sciences. 4:27-31 (2013).
Bayne, "Correlation of clinical performance with 'in vitro tests' of restorative dental materials that use polymer-based matrices," Dent Mater. 28:52-71 (2012).
English translation of Chinese Patent Application No. 201080021771.9, dated Nov. 3, 2014 (8 pages).

\* cited by examiner

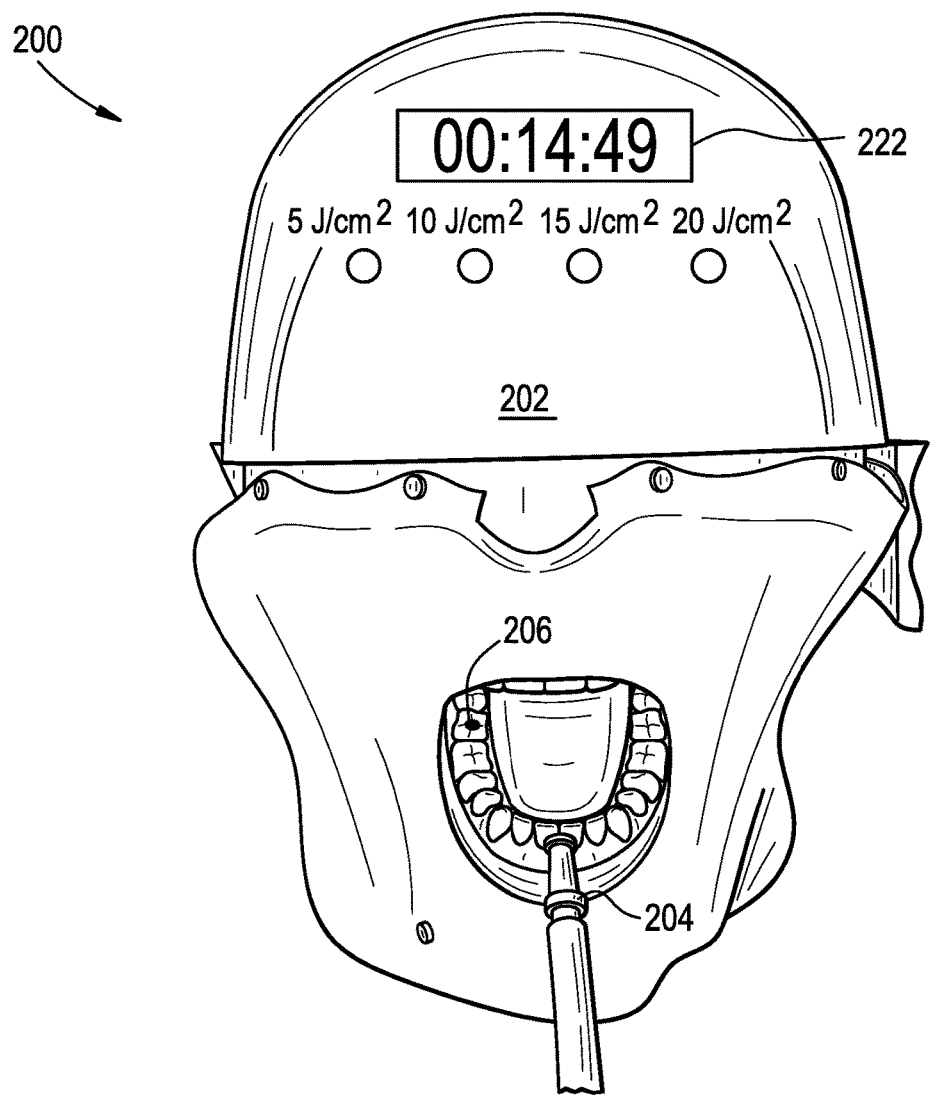

ANOVA Table for Energy Delivered

| | DF | Sum of Squares | Mean Square | F-Value | P-Value | Lambda | Power |
|---|---|---|---|---|---|---|---|
| TOOTH | 3 | 1239.030 | 413.010 | 39.791 | <.0001 | 119.374 | 1.000 |
| Residual | 44 | 456.694 | 10.379 | | | | |

Means Table for Energy Delivered
Effect: TOOTH

| | Count | Mean | Std. Dev. | Std. Err. |
|---|---|---|---|---|
| Class I | 12 | 8.442 | 2.188 | .632 |
| Class III Lingual | 12 | 12.771 | 2.664 | .769 |
| Class V DB | 12 | 3.290 | 3.248 | .938 |
| Occlusal | 12 | 16.976 | 4.368 | 1.261 |

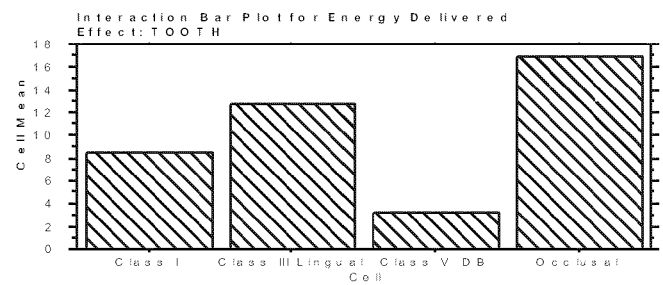

Fisher's PLSD for Energy Delivered
Effect: TOOTH
Significance Level: 5 %

| | Mean Diff. | Crit. Diff | P-Value | |
|---|---|---|---|---|
| Class I, Class III Lingual | -4.330 | 2.651 | .0020 | S |
| Class I, Class V DB | 5.152 | 2.651 | .0003 | S |
| Class I, Occlusal | -8.534 | 2.651 | <.0001 | S |
| Class III Lingual, Class V DB | 9.481 | 2.651 | <.0001 | S |
| Class III Lingual, Occlusal | -4.205 | 2.651 | .0026 | S |
| Class V DB, Occlusal | -13.686 | 2.651 | <.0001 | S |

FIG. 9A

ANOVA Table for Energy Delivered

| | DF | Sum of Squares | Mean Square | F-Value | P-Value | Lambda | Power |
|---|---|---|---|---|---|---|---|
| DENTIST | 2 | 7.184 | 3.592 | .159 | .8549 | .319 | .068 |
| Residual | 9 | 202.709 | 22.523 | | | | |

Means Table for Energy Delivered
Effect: DENTIST

| | Count | Mean | Std. Dev. | Std. Err. |
|---|---|---|---|---|
| 1 | 4 | 17.306 | 5.534 | 2.767 |
| 2 | 4 | 17.715 | 5.294 | 2.647 |
| 3 | 4 | 15.908 | 2.987 | 1.493 |

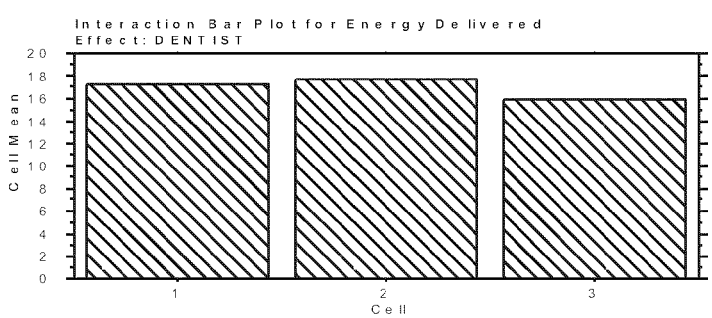

Fisher's PLSD for Energy Delivered
Effect: DENTIST
Significance Level: 5 %

| | Mean Diff. | Crit. Diff | P-Value |
|---|---|---|---|
| 1, 2 | -.408 | 7.591 | .9058 |
| 1, 3 | 1.398 | 7.591 | .6866 |
| 2, 3 | 1.807 | 7.591 | .6033 |

FIG. 9B

Final Results

| | Anterior | Posterior | Overall |
|---|---|---|---|
| Light #1 | 13.25 +/- 0.00 | 4.52 +/- 2.87 | 5.97 |
| Light #2 | 7.96 +/- 0.00 | 5.64 +/- 1.24 | 6.11 |
| Light #3 | 6.61 +/- 0.00 | 7.28 +/- 2.28 | 7.12 |
| Light #4 | 8.41 +/- 0.00 | 4.21 +/- 1.66 | 5.26 |

FIG. 10A

Mean +/- S.D. Energy Delivered

| | Distance to Detector 0mm | Distance to Detector 4.5mm | Overall |
|---|---|---|---|
| Light #1 | 10.51 +/- 1.21 | 2.92 +/- 1.98 | 6.72 |
| Light #2 | 17.56 +/- 1.12 | 3.01 +/- 2.34 | 10.29 |
| Light #3 | 11.37 +/- 0.26 | 3.12 +/- 3.48 | 7.25 |
| Light #4 | 9.80 +/- 0.29 | 4.08 +/- 4.02 | 6.94 |

METHOD AND SYSTEM FOR MEASUREMENT OF CURING ENERGY DELIVERED DURING SIMULATED DENTAL RESTORATIONS

CROSS REFERENCE TO RELATED APPLICATIONS

This application claims the benefit of U.S. Provisional Patent Application No. 61/168,039 entitled "METHOD AND SYSTEM FOR MEASUREMENT OF CURING ENERGY DELIVERED DURING SIMULATED DENTAL RESTORATIONS" filed on Apr. 9, 2009, and which is hereby expressly incorporated herein by reference in its entirety.

FIELD OF THE INVENTION

The present invention relates generally to quantitatively monitor the amount of curing energy delivered during simulated dental restorations. More particularly, the present invention relates to measurement of energy delivered as simulated dental restorations are light cured.

BACKGROUND OF THE INVENTION

According to the World Health Organization, tooth decay is one of the world's most prevalent health problems. It has been estimated that 90% of people in the United States have at least one cavity. Children and senior citizens are the two groups of people at highest risk. Dental resin restorations represent a significant market, but over 60% of all restorative dentistry is for the replacement of restorations. Placement of resin restorations is technique sensitive and, therefore, must be placed properly to deliver the best health care to patients. The most common cause of failure of resin restorations is secondary caries (tooth decay) due to microleakage around the restoration, followed by restoration fracture, and marginal defects. These failures may be due to the fact that the resin restoration was inadequately polymerized and did not reach its intended physical properties.

Dental students, dentists and dental auxiliaries are evaluated on their ability to prepare teeth and on the final restoration of the tooth. However, the ability of the operator (for example, a dentist, or a dental student) to deliver sufficient useful curing energy to adequately cure a restoration is not readily measurable, and it is not feasible to detect visually or tactily if the resin restoration is adequately cured.

Inadequately cured resins will result in reduced physical properties of the restoration, reduced bond strengths, increased wear and breakdown at the margins of the restoration, decreased biocompatibility, and increased DNA damage from the leachates. These leachates can include bisphenol A diglycidylether methacrylate (Bis-GMA), tetraethyleneglycol dimethacrylate (TEGDMA), 1,6-bis (methacryloxy-2-ethoxycarbonylamino)-2,4,4-trimethyl-hexane (UDM), 2,2-bis(4-(2-Methacryloxyethoxy)phenyl-propane (bis-EMA), and bisphenol A with the total monomer of BisGMA and TEGDMA eluted reported to range from 8.75 to 27.97 ppm. In vitro studies have shown that resin components can evoke either immunosuppression or immunostimulation on mitogen-driven proliferation of purified T-lymphocytes and spleen cells. Conversely, too much curing energy delivered to the restoration may cause an unnecessary and unacceptable temperature increase in the tooth and surrounding oral tissues.

SUMMARY OF THE INVENTION

The drawbacks associated with current methods of training and evaluating dentists in curing a restoration can be overcome by providing a method and system that measures and calculates the amount of curing energy delivered during the curing of simulated dental restorations. This can show the operator whether or not they are delivering sufficient curing energy to a restoration in real-time.

In some aspects, there is provided a system for real-time measurement of curing energy delivered to a simulated dental restoration from a source of curing energy. The system comprises a detector, a processor, software to analyze the data and a display. The detector measures at a location within the simulated dental restoration an amount of the curing energy delivered by the curing energy source. The process and software analyses the data and the display displays the measured amount of energy and useful curing in real-time.

In some embodiments, the system further comprises a dental mannequin having artificial cheeks, lips, a tongue, and a variable jaw opening for receiving at least one simulated tooth for simulating the dental restoration. The simulated tooth can be made from material having substantially similar optical properties of a tooth.

In some embodiments, the detector is placed within the at least one simulated tooth at a predetermined depth for simulating a tooth cavity condition. A curable material can be placed within the at least one simulated tooth for exposing the curable material to the curing energy to simulate the dental restoration. The detector can be located outside the curable material for measuring the amount of the curing energy delivered to the curable material. The detector can be a pyroelectric detector, photodiode, a charged-coupled device photodetector (CCD photodetector) or a spectroradiometer or any type of energy detector capable of detecting photons in the 200 to 700 nm range.

In some embodiments, a temperature sensor is provided. The temperature sensor can be placed on a tooth or in the gums adjacent to the tooth simulating a tooth cavity condition. When curing a restoration using improper technique the curing energy can cause an unacceptable rise in the tooth pulp or gingival temperature leading to pulpal or gingival damage and inflammatory response. Thus, the temperature sensor can report a change in temperature during a simulated resin restoration and that data can be used to evaluate the operator and/or the curing energy source for its efficiency in curing a restoration without harming adjacent areas, such as the tooth pulp, oral tissues and gingival tissues that surround the tooth whose resin is being cured.

In some embodiments, an intra-oral camera is provided within the dental mannequin. The intra-oral camera can be used for capturing still images or real-time video of the light curing technique. The camera images or video can also be enhanced with a timestamp for correlating the images or video with the real-time curing-energy data.

In some embodiments, the system further comprises a processor that can optimize the amount of curing energy delivered based on a predetermined amount of energy to adequately cure the simulated dental restoration.

The system can also include a database to store a user profile for individual users. The user profile can include an ability of the user to deliver the predetermined amount of energy to the simulated dental restoration using different light energy sources. The user profile can also include the ability of the user to deliver the predetermined amount of energy to at least two locations in the simulated dental restoration. The data in the user profiles can be used to rank a user against other users.

The database can further store a curing energy source profile for each curing energy source. The curing energy source profile can include an ability of each curing energy source to deliver the predetermined amount of energy to the simulated dental restoration. The curing energy source can be ranked in comparison to other curing energy sources in the database based on the curing energy source profiles.

In some aspects, there are provided methods for real-time reporting of curing energy delivered to a simulated dental restoration, the method comprising: providing curing energy to the simulated dental restoration; measuring the amount of the curing energy delivered at a detector located within the simulated dental restoration; recording the process using real-time video as energy is delivered; measuring the temperature changes as energy is delivered using detectors located within the tooth and gums; and, displaying the measured amount of energy delivered in real-time.

In some embodiments, the method further comprises providing a curable material within the at least one simulated tooth; and, exposing the curable material to the curing energy to simulate the dental restoration. This curable material can then be removed from the simulated tooth and subjected to physical and chemical tests. Based on the results of these tests, the method comprises optimizing the time required to deliver the required amount of curing energy that needs to be delivered to the simulated restoration.

In yet another embodiment, the method further comprises determining the time required to deliver the required amount of energy to the simulated dental restoration based on measuring an amount of energy required to adequately cure a curable material placed in a tooth with a clinically relevant reflective background surface.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIG. 2 is a photograph of a system for real-time measurement of curing energy delivered in a simulated dental restoration according to an embodiment;

FIGS. 6A and 6B show user interfaces illustrating user identity, location of a simulated tooth (FIG. 6A) and identification curing energy source (FIG. 6B) according to an embodiment;

FIGS. 9A and 9B show statistical analyses of curing energy delivered at different locations of a simulated tooth (FIG. 9A) and by different users (FIG. 9B);

FIGS. 10A and 10B show user interfaces illustrating ranking of the overall performance of several curing energy sources at different locations of a simulated tooth (FIG. 10A) and at various distances between the curing energy source and a detector placed in the simulated tooth (FIG. 10B);

FIG. 19C is a user interface showing all data across several trial runs by a user.

DETAILED DESCRIPTION

Figure 1A:
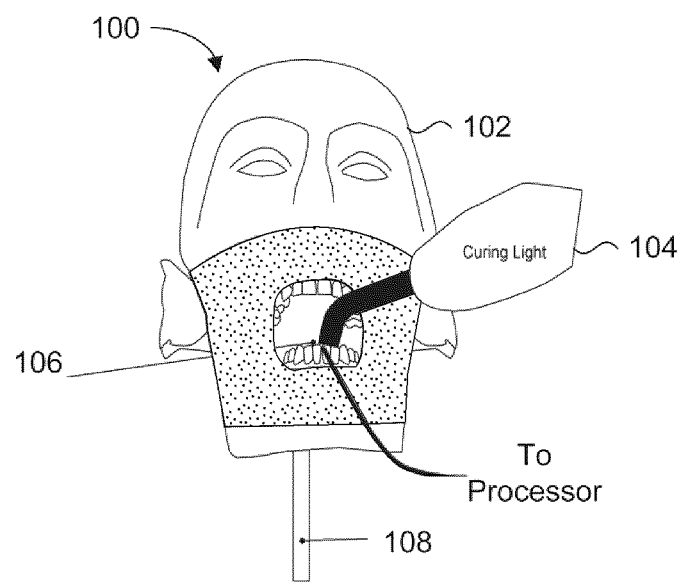
FIG. 1A is a schematic representation of a system for real-time measurement of energy delivered to cure a simulated dental restoration according to an embodiment.

Light curable resins (white fillings) used by dentists to restore teeth require sufficient curing energy, for example, light energy, to adequately polymerize the resin filling in the tooth. In a recent study at Dalhousie University's School of Dentistry, 50% of trainees were delivering less than an adequate amount of light to resin restorations. Although resin manufacturers provide approximate curing times for their light curing materials, the operator does not readily know if they are actually delivering sufficient light energy to effectively cure the restorations in the mouth so that they are safe and durable. This is partly because the light curing devices available to dentists deliver very different light intensities, spectral outputs, and are of different shapes and designs. Furthermore, the angle and distance from the light source to the resin affects the amount of useful light actually received by the resin.

Typically, a dental curing light is used as an energy source to cure resin based restorations. Examples of curing lights include laser, LED, halogen, or plasma arc light sources, which are available in various shapes and sizes. A variety of light meters are available to dentists to test the output from their curing lights, but these meters only test the output of the light in a bench-top setting and are unable to test or measure the actual amount of light a restoration receives in the mouth.

Presently, a dentist can measure the output from their curing light using an external sensor outside of the mouth primarily to check whether the curing light is functioning correctly under ideal circumstances. In reality, this measurement does not provide any indication of the amount of curing energy the curing light delivers to a restoration in the mouth. Moreover, the operator cannot monitor and optimize, in real-time, how much energy they are delivering to a restoration in the mouth.

In the pilot study at Dalhousie University, the irradiance received by a Class I restoration in a molar tooth in one location in a dental mannequin head was collected using a commercially available spectroradiometer. The data was analyzed at a later date to obtain measurements of the actual amount of energy delivered to the simulated restoration. To simulate clinical reality, a mannequin head was attached to a dental chair in the dental clinic. Three different curing lights were used in the study and the irradiance ($mW/cm^2$) received by the restoration was recorded throughout the light curing process to calculate the energy ($J/cm^2$) delivered by each volunteer to the simulated restoration. Manufacturers and researchers recommend delivering about 10 to 20 $J/cm^2$ of energy to the restoration, but the amount of light energy delivered by the volunteers ranged from 2 $J/cm^2$ (inadequate) to 12 $J/cm^2$ (barely adequate). There was also a significant difference in the energy delivered by the three lights ($p<0.01$). It was concluded that many dental restorations probably receive much less energy in a typical dental setting than previously thought.

As discussed earlier, insufficient curing energy may result in reduced physical properties, reduced bond strength, increased wear and breakdown at the margins of the restoration, decreased biocompatibility, and increased DNA damage from the leachates. The leachates can include bisphenol A diglycidylether methacrylate (Bis-GMA), tetraethyleneglycol dimethacrylate (TEGDMA), 1,6-bis(methacryloxy-2-ethoxycarbonylamino)-2,4,4-trimethylhexane (UDMA), 2,2-bis(4-(2-Methacryloxyethoxy)phenylpropane (bis-EMA), and bisphenol A with the total monomer of BisGMA and TEGDMA eluted reported to range from 8.75 to 27.97 ppm. In vitro studies have shown that resin components can evoke either immunosuppression or immunostimulation on mitogen-driven proliferation of purified T-lymphocytes and spleen cells. Conversely, too much energy delivered to the restoration may cause an unnecessary and unacceptable temperature increase in the tooth.

The preliminary tests demonstrate that almost all dental professionals (dentists, dental hygienists, trainees and assistants) can benefit from instruction on how to optimally deliver curing energy to the restoration, for example, correctly positioning the curing light to deliver an adequate amount of light to the resin.

Currently available sensor systems do not provide the user with real-time information about the energy delivered to the restoration, use expensive detection methods to determine when the resin is cured, or rely on external detectors to estimate the time required for curing a resin. Therefore, there is a need for a device that measures the amount of actual curing light energy received by a dental restoration in the mouth and provides this information quickly back to the user.

Generally, in some aspects of the system described herein, there is provided a system for real-time measurement of curing energy delivered in a simulated dental restoration. A curing source provides curing energy to the simulated dental restoration. An amount of the curing energy delivered is measured at a location within the simulated dental restoration by a detector and is displayed using a display in real-time. As used herein the phrases "real time," "substantially real time," "instant," "instantly," and the like refer relative periods of time that are generally imperceptible to the user, or the time it takes for a step to be processed and displayed.

The dental restoration can be simulated in a dental mannequin having artificial cheeks, lips, a tongue and a jaw for receiving at least one simulated tooth for restoration. The construction of the mannequin can be such that it closely simulates a patient requiring dental restoration. That is, the jaws can be movable to mimic a patient's jaw movements; the cheeks, lips and tongue can create the typical environment a dentist would encounter while treating a patient for restorative work. Additionally, the simulated tooth can be made from material, such as a dental resin composite, so as to match as closely as possible or to have substantially similar optical properties of a tooth.

In some embodiments, one or more photo-detectors located in the mouth of a mannequin are used to measure the amount of curing light energy the user is delivering to a simulated dental restoration. The measurements can be made at different depths within the curable material in order to simulate different types of cavities. The operator or user can see in real-time if they are delivering sufficient energy to adequately polymerize the resin filling, and they can compare their results with other users. As used herein terms referring to curing light energy, curing energy, energy used to cure a restoration, etc. refer to any type of energy delivered from any energy source used in curing dental restorations. Accordingly, terms used herein referring to measuring or detecting curing light energy, curing energy, energy used to cure a restoration, etc. refer to any suitable detector for detecting or measuring such energy. In some embodiments of the technology the energy source can deliver electromagnetic radiation, e.g. light, to cure the material used in the restoration or simulated in the restoration, and detectors suitable for detecting and/or measuring electromagnetic radiation, e.g., light, are used to detect the electromagnetic radiation. For example, measuring curing energy can refer to measuring electromagnetic radiation by measuring irradiance, power, spectral radiant flux, etc.

The system, can record the amount of energy an operator actually delivers to a simulated resin restoration in the mouth. The information can be recorded and displayed in real-time and can be used to optimize the exposure time based on a predetermined amount of energy to be delivered to the simulated dental restoration.

In some embodiments, the detector used for measuring the amount of curing energy delivered to the simulated dental restoration is a sensor connected to a spectroradiometer. Alternatively, any suitable light or power detector, such as a pyroelectric detector, photodiode or a CCD photodetector, can be used for this purpose. The processor transforms the power values recorded by the detectors into a real-time energy delivered output and calculates the time required to deliver predetermined amounts of energy to the simulated dental restoration.

The system can also include an analog/digital converter for converting analog signals from the detector to digital signals for further processing by the processor and a custom power meter. The output from the processor can be provided via Bluetooth, USB ports, a system bus, or direct connection to a computer or a PDA or any other suitable display (audio, visual, or mechanical). The energy received by the simulated dental restoration in real-time and via an intra oral video of the procedure can be displayed to the operator.

A processor connected to the detector can be configured to measure the amount of curing light energy an operator actually delivered to a simulated resin restoration in the mouth in real-time. The processor can be further configured to determine an optimum duration for delivering the curing energy based on a predetermined amount of energy required to cure the simulated dental restoration. The processor can be configured to provide instant feedback to operators on their ability to deliver sufficient light to the simulated tooth. In addition, the processor can be configured to provide the results of operators ranked against previous users. The processor can also be configured to rank the ability of operators to deliver sufficient light in multiple locations using different brands of light in the simulated mouth. Similarly, the processor can record curing energy source profiles and different curing energy sources can also be comparatively ranked.

In some aspects, there is provided a method for real-time measurement of curing energy delivered to a simulated dental restoration, the method comprising: providing curing energy to the simulated dental restoration; measuring an amount of the curing energy delivered at a detector located within the simulated dental restoration; and, displaying the measured amount of the curing energy in real-time.

In some embodiments, the method further comprises providing a curable material within the at least one simulated tooth; and, exposing the curable material to the curing energy to simulate the dental restoration. Additionally, the method comprises optimizing the curing energy delivered based on a predetermined total amount of energy to be delivered to the simulated restoration.

In some embodiments, the method further comprises determining the amount of time that is needed to deliver an amount of energy to equal the predetermined amount of energy delivered to the simulated dental restoration based on measuring an amount of energy required to adequately cure a curable material placed in a tooth with a clinically relevant reflective background surface.

The system, in some aspects, can serve as a demonstration platform to demonstrate curing lights at continuing education courses, trade shows and conferences for marketing purposes. Additionally, the system can be used to develop curing lights that deliver an adequate amount of energy to a restoration in the mouth. Newly developed curing lights can be tested on this system and intra oral curing times for the curing lights can be determined. Furthermore, the system can aid in the ergonomic design and development of curing lights that can more easily deliver sufficient light to dental restorations. The ergonomic designs of the wide variety of curing light sources currently available can be maximized for effective light delivery in the clinical setting using the system described herein.

A schematic representation of the system 100 for real-time measurement of curing energy delivered in a simulated dental restoration according to some embodiments is shown in FIG. 1A. The system comprises a mannequin head 102 having at least one tooth for simulating the dental restoration. The mannequin head is connected to a dental chair, for example by using a pole 108 or strap.

Figure 1B:
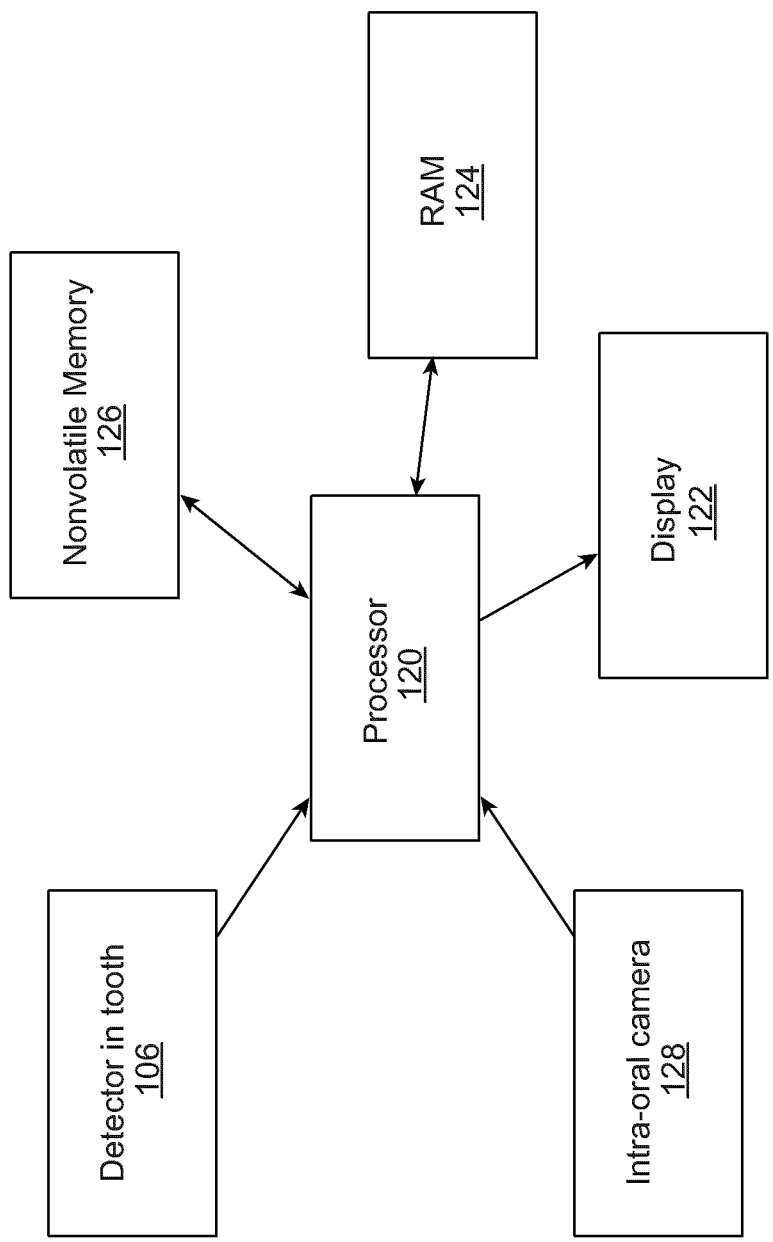
FIG. 1B is a schematic block diagram of a system described herein.

FIG. 1B is a schematic block diagram of the system described herein. A curing light 104 (FIG. 1A) provides curing energy to a tooth having a detector 106 to measure the curing energy delivered to the simulated dental restoration by the curing light. The detector 106 is connected to a processor 120, e.g., analog to digital converter or microprocessor, etc., for processing the data received by the detector for use with other components of the system. For example, the processor can convert electronic signals received from the detector to recognizable energy values for presentation to an operator on display 122. The electronic signals received from the processor are processed at the direction of software instructions that are stored, for example in non-volatile memory 126, and loaded into RAM 124.

The processor can also temporarily store application modules, or data received from the detector 106, the temperature sensor or intra-oral camera 128 in the RAM 124. The intra-oral camera 128 can be used to record video or still images of an operator performing a simulated restoration and the processor can process the video or still images, add a timestamp and output the images to display 122. The processor can also be configured to output to the display 122, a variety of other graphs, measurements, calculations and values, as described in greater detail herein, based on instructions provided by the software.

It should be appreciated that one or more of the system components can be removed or substituted depending on specific embodiments, each of which is encompassed by the present technology.

In some embodiments, as shown in FIG. 2, the system 200 can include an integrated head 202, such as a plastic head or a mask, for the real-time measurement of curing energy delivered to a simulated dental restoration. In this embodiment, the curing energy source 204 delivers curing energy to a detector 206 located in a simulated tooth of the head 202. The output of the detector 206 is coupled to a digital readout 222 for real-time display of the amount of curing energy provided to the simulated dental restoration. The digital readout 222 can also provide instantaneous feedback to the operator to show if the operator has delivered adequate amount of curing energy to the dental restoration using, for example, colored display lights indicative of curing energy delivered to the detector and the exposure time from the curing light. Due to the simplicity and integrated construction, these embodiments are ideally suited as a demonstration platform to demonstrate curing lights at trade shows, conferences etc. for marketing purposes.

Figure 3A:
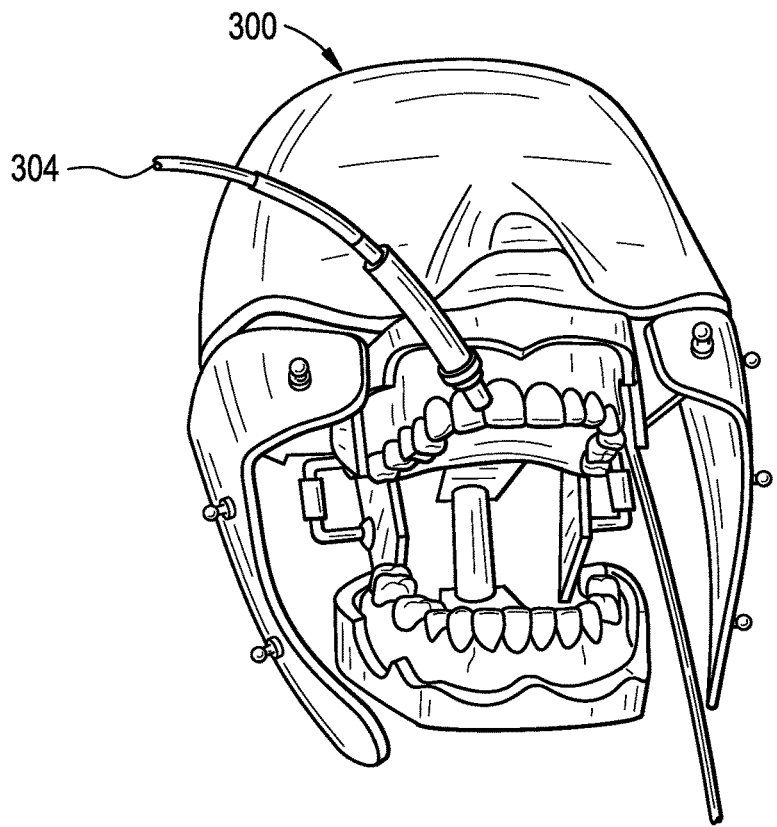
FIG. 3A is a photograph of a dental mannequin used for a simulated dental restoration according to another embodiment.

More sophisticated embodiments for the real-time measurement of curing energy delivered in a simulated dental restoration are shown in FIG. 3A. In the system 300, a dental mannequin having artificial cheeks, and a jaw for receiving at least one simulated tooth is shown. The construction of the mannequin is such that it closely simulates a patient requiring dental restoration. That is, the jaws can be movable to mimic a patient's jaw movements; the cheeks, lips and tongue (not shown) create the typical environment a dentist would encounter while treating a patient. The curing energy source delivers curing energy to detectors 304 and/or 306 located in a simulated tooth as shown in FIG. 3B.

Figure 3B:
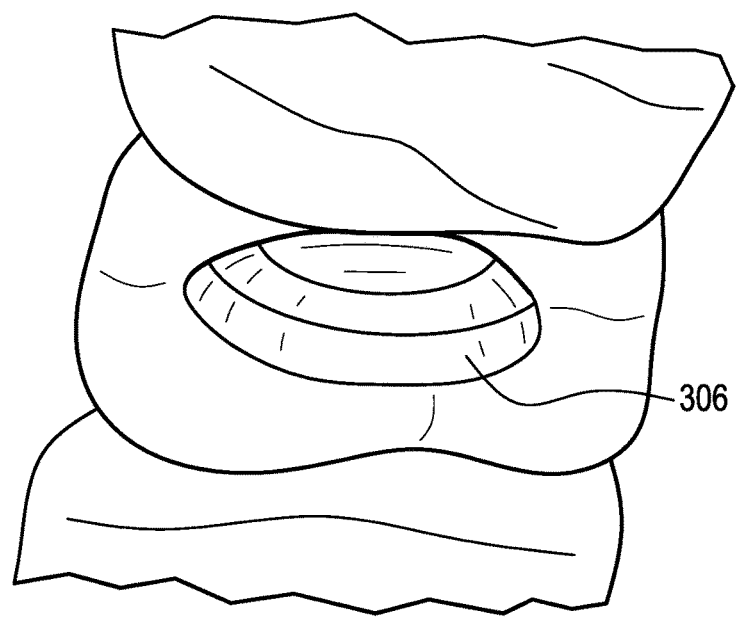
FIG. 3B is a photograph of a simulated tooth and sensor for the simulated dental restoration according to the embodiment of FIG. 3A.

In the embodiments shown in FIGS. 3A and 3B, the dental restoration can be simulated in any location in the mouth. The tooth with the detector can be placed in different locations (anterior or posterior) on the jaw for simulating dental restoration of different teeth in a patient. Due to its flexibility and robustness, these embodiments can be used as a teaching/training tool in health professional schools and the like.

In these embodiments, the system is spectroradiometer-based and uses photo-detectors inside mannequin teeth to detect the amount of energy received by the simulated dental restoration in a tooth as shown in FIGS. 3A and 3B. The photo-detectors are attached via fiber optic cables to a spectroradiometer and the received data is processed to obtain a real-time energy and spectral output measurement. The real-time readout is displayed on a suitable display such as that of a computer (not shown in FIGS. 3A and 3B).

Figure 4A:
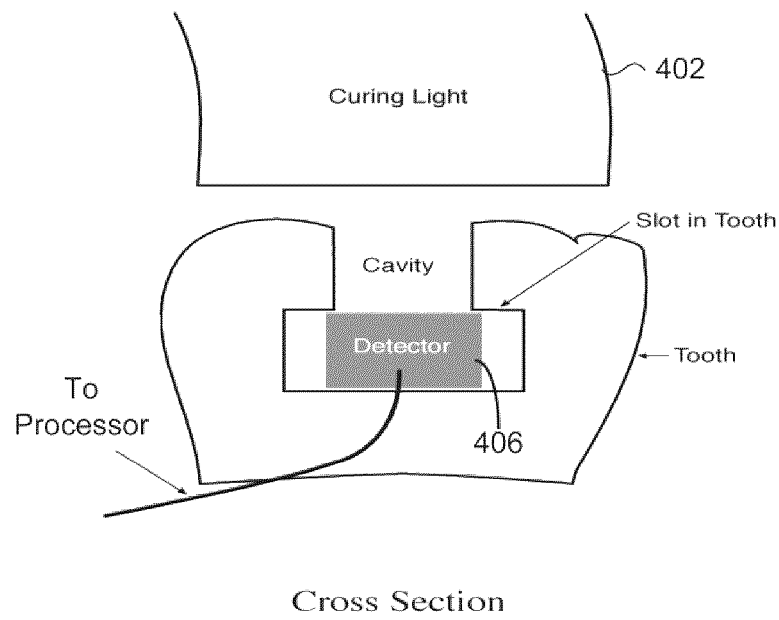
FIG. 4A is a schematic representation of a cross-section of the simulated tooth used for the simulated dental restoration according to the embodiment of FIG. 3A.

FIG. 4A shows a schematic representation of a cross-section of the simulated tooth used for the simulated dental restoration, for example, in the embodiment of FIGS. 3A and 3B. The detector 406 is placed in a slot in the cavity of the simulated tooth and measures the curing energy delivered by the curing light 402. The placement of the detector 406 can be controlled to be at various depths within the cavity to simulate different tooth cavity shapes encountered in real life.

Figure 4B:
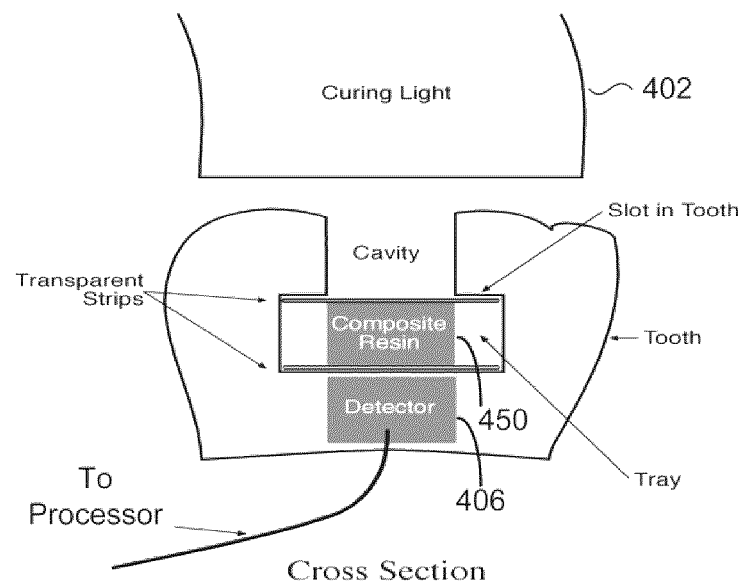
FIG. 4B is a schematic representation of a cross-section of a simulated tooth with a curable material used for a simulated dental restoration according to yet another embodiment.

The system 300 of FIG. 3A can be modified, in an embodiment shown in FIG. 4B, to receive a curable material 450 such as a composite resin that is used for dental restorations. The curing material 450 can be placed in the cavity above the detector 406. The curing material is placed between transparent strips for allowing the curing light through. The transparent strips prevent formation of an air-inhibited layer on the resin and provide ease of handling. Thus, the curing light energy that is delivered to the top of a restoration and through to the bottom of a restoration in a tooth can be measured.

Figures 5A, 5B:
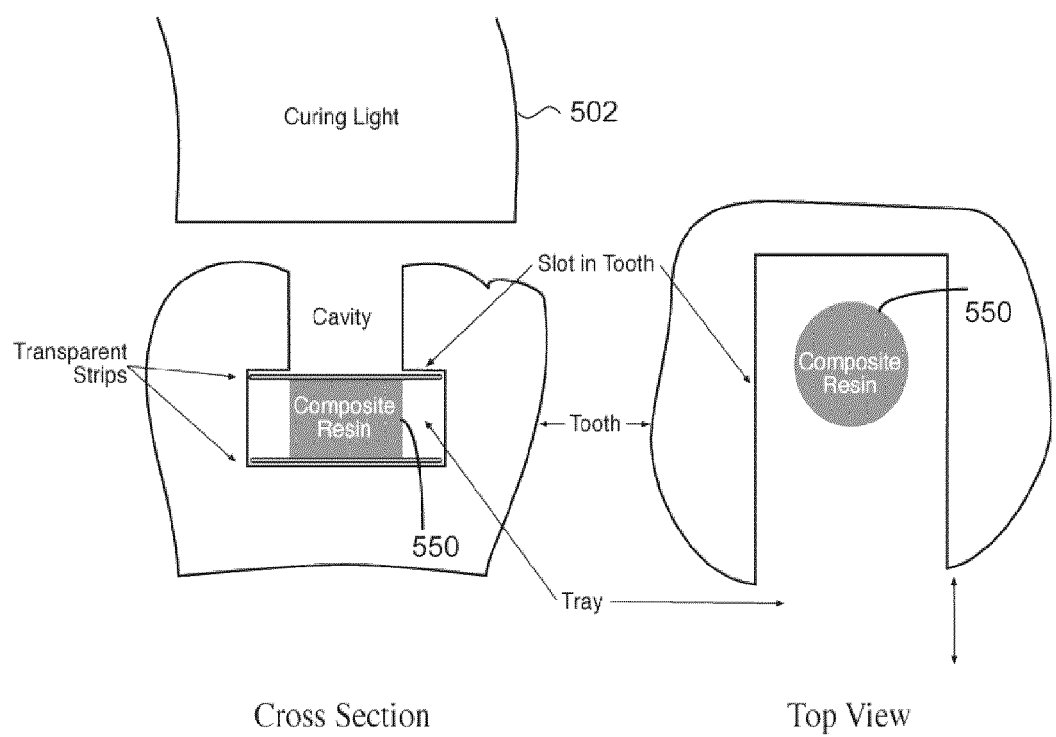
FIG. 5A is a cross-section of a simulated tooth with a curable material used for a simulated dental restoration according to a further embodiment.
FIG. 5B is a top view of the simulated tooth with the curable material used for the simulated dental restoration according to the embodiment of FIG. 5A.

In yet another embodiment, shown FIGS. 5A and 5B, the composite resin 550 is placed in a tray that slides into the tooth. The curing light 502 can cure the composite resin in a simulated dental restoration. The cured composite resin can then be removed from the tooth and the cured resin specimen can be subjected to various chemical and physical property tests (see experiment below) to determine the effectiveness of the curing light 502. Thus, actual performance of different dental curing lights to cure different brands and types of dental composite resins in various locations in the simulated mouth can be determined.

Figure 5C:
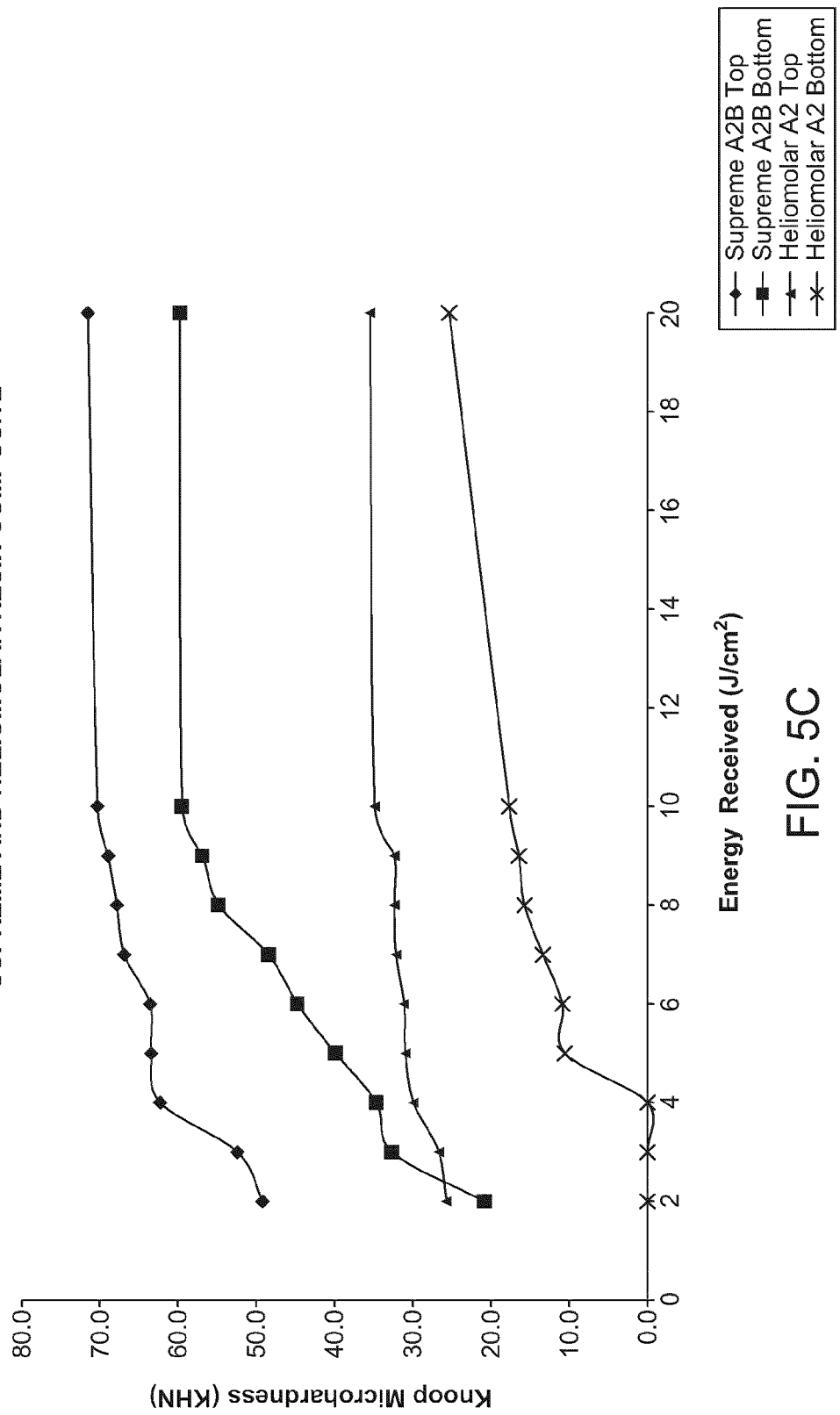
FIG. 5C illustrates data derived from resin samples cured within a removable tray.

FIG. 5C illustrates data derived from resin samples cured within a removable tray.

Two resin composites were cured with different energy levels and the hardness of the two samples were measured at the top and bottom of the samples. As illustrated the FILTEK SUPREME dental resin by 3M, St. Paul, Minn., achieved a Knoop Microhardness of approximately 70 KHM on the top of the resin after receiving approximately 10 $J/cm^2$ of energy and achieved a Knoop Microhardness of approximately 60 KHM on the bottom of the resin after receiving about the same amount of energy. However, the HELIOMOLAR dental resin by Ivoclar Vivadent of Amherst, N.Y., achieved a Microhardness of approximately 30 KHM on the top of the resin also after receiving approximately 10 $J/cm^2$ of energy, while only achieving a Microhardness approximately 20 KHN on the bottom after receiving approximately 20 $J/cm^2$ of energy.

As described earlier, the processor connected to the detector can be configured to measure the amount of curing light energy an operator actually delivered to a simulated resin restoration in the mouth in real-time. The processor can be configured using appropriate processor implemented instructions, e.g., software. The software can instruct the processor to convert digital signals received from the detector into energy values understandable by an operator. The software can further configure the processor to display the energy values on a display. In some aspects, it is especially contemplated that the processor will output real-time values corresponding to the amount of energy actually delivered to the simulated resin restoration, and correspondingly detected by the detector. Such real-time values can be further used to calculate a remaining duration for which the curing energy source should be applied in order to fully cure the simulated resin restoration. The remaining duration can be calculated by comparing the rate at which energy is being delivered to the simulated resin restoration and the amount of energy already delivered with the amount of energy needed to cure the simulated resin.

Figures 6A, 6B:
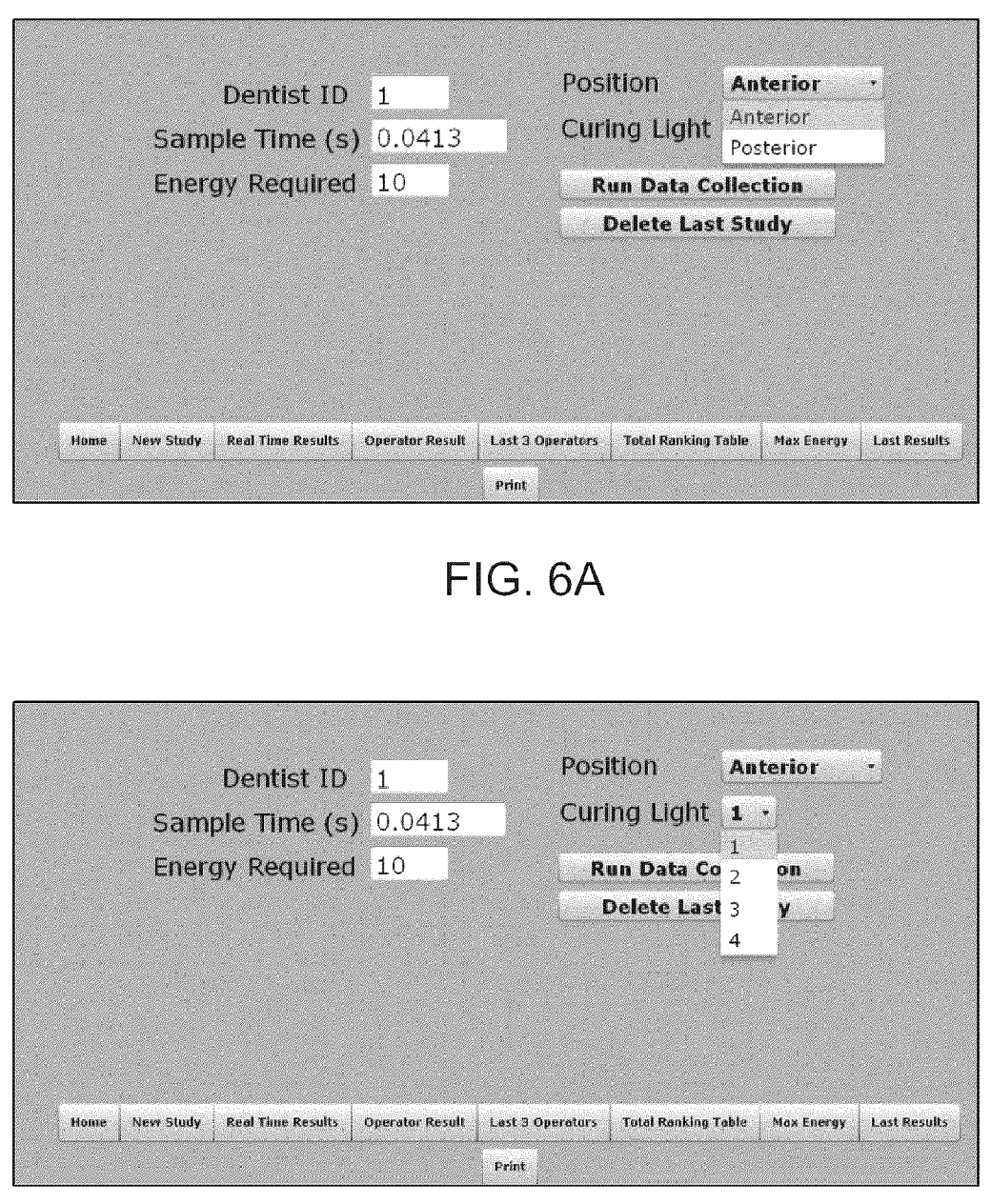

The software can further instruct the processor to store, in a database, a user profile including an ability of a user to deliver the predetermined amount of energy to the simulated dental restoration. The software can also provide suitable user interfaces for conveying the real-time measurements to a user in various forms. FIGS. 6A and 6B show user interfaces illustrating user identity, location of a simulated tooth, for example, anterior and posterior (FIG. 6A) and identification curing energy source, for example, curing light #1, #2, #3, and #4 (FIG. 6B).

Figure 7A:
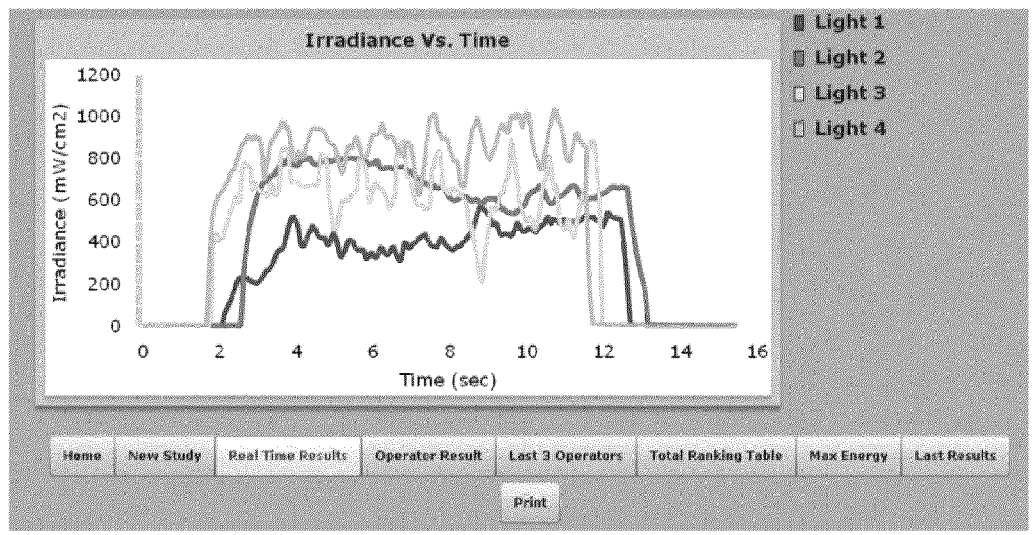
FIGS. 7A and 7B show user interfaces illustrating comparison of curing light irradiance delivered over time by several curing energy sources (FIG. 7A) and comparison of curing energy delivered by several curing energy sources against a reference value (FIG. 7B)
Figure 7B:
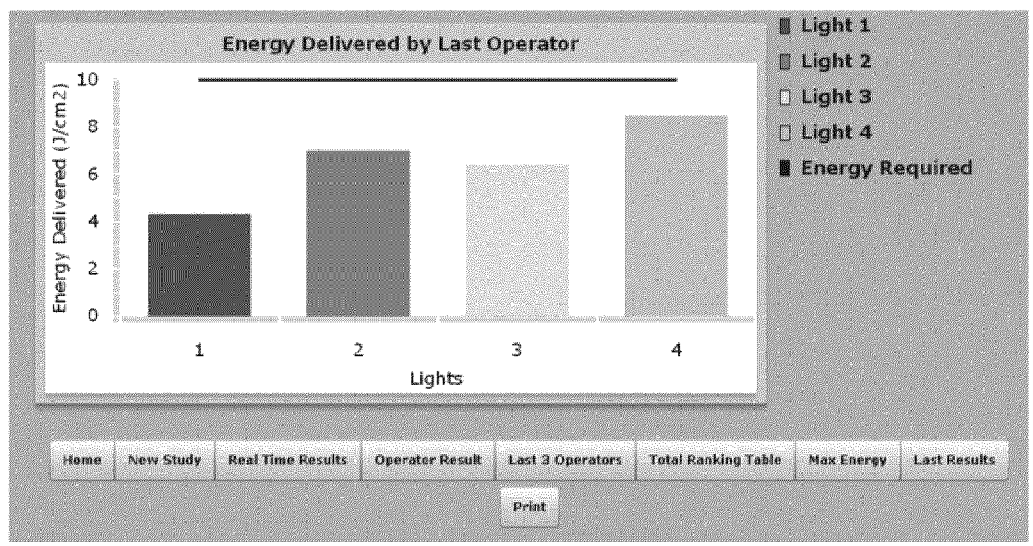
Figure 8A:
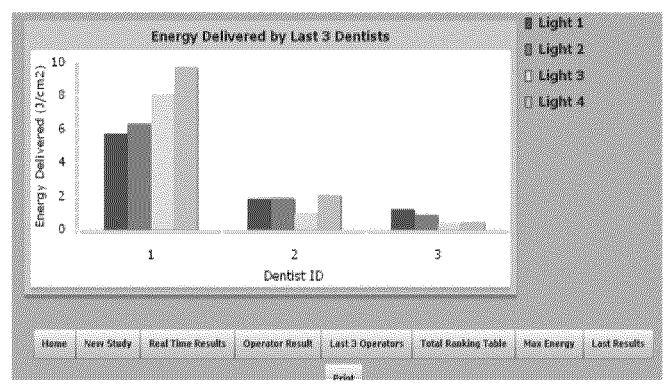
FIGS. 8A and 8B show user interfaces illustrating comparison curing energy delivered by several curing energy sources by different users at location 1 (FIG. 8A) and at location 2 (FIG. 8B)
Figure 8B:
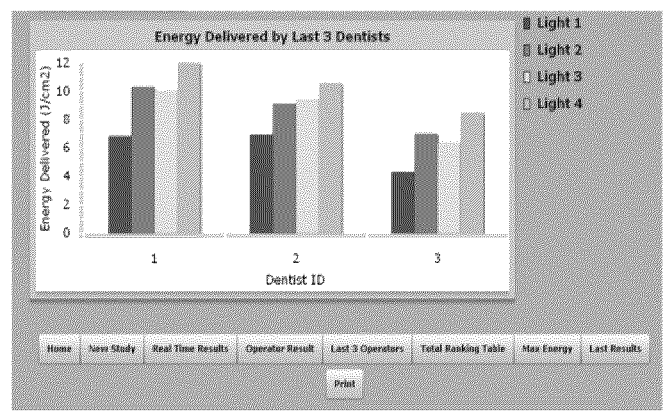

In addition, the software can further instruct the processor to provide user interfaces for comparison of curing light irradiance delivered over time by several curing energy sources as shown in FIG. 7A and for comparison of curing energy delivered by several curing energy sources against a reference value as shown in FIG. 7B. FIGS. 8A and 8B show user interfaces for comparison of curing energy delivered by several curing energy sources by different users at location 1 and at location 2, respectively. Statistical analyses of curing energy delivered at different locations of a simulated tooth is shown in FIG. 9A and that of curing energy delivered by different users is shown in FIG. 9B.

The software can further instruct the processor to provide statistical analyses of the performance of various users and can rank a user in comparison to other users in the database based on the user profiles. Furthermore, the software can cause a curing energy source profile to be stored in the database, located either internally or at a remote location accessible via the Internet, including an ability of the curing energy source to deliver the predetermined amount of energy to the simulated dental restoration. The software can further instruct the processor to rank the curing energy source in comparison to other curing energy sources in the database based on the curing energy source profiles. FIGS. 10A and 10B show user interfaces illustrating ranking of the overall performance of several curing energy sources at different locations of a simulated tooth (FIG. 10A) and at various distances between the curing energy source and a detector placed in the simulated tooth (FIG. 10B).

Figure 11:
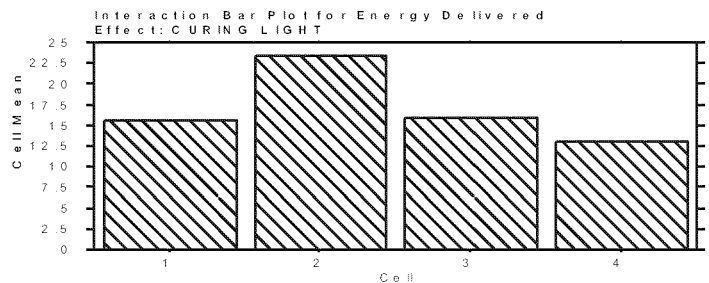
FIG. 11 shows statistical analyses of curing energy delivered by several curing energy sources.

FIG. 11 shows statistical analyses of curing energy delivered by several curing energy sources.

Figure 12:
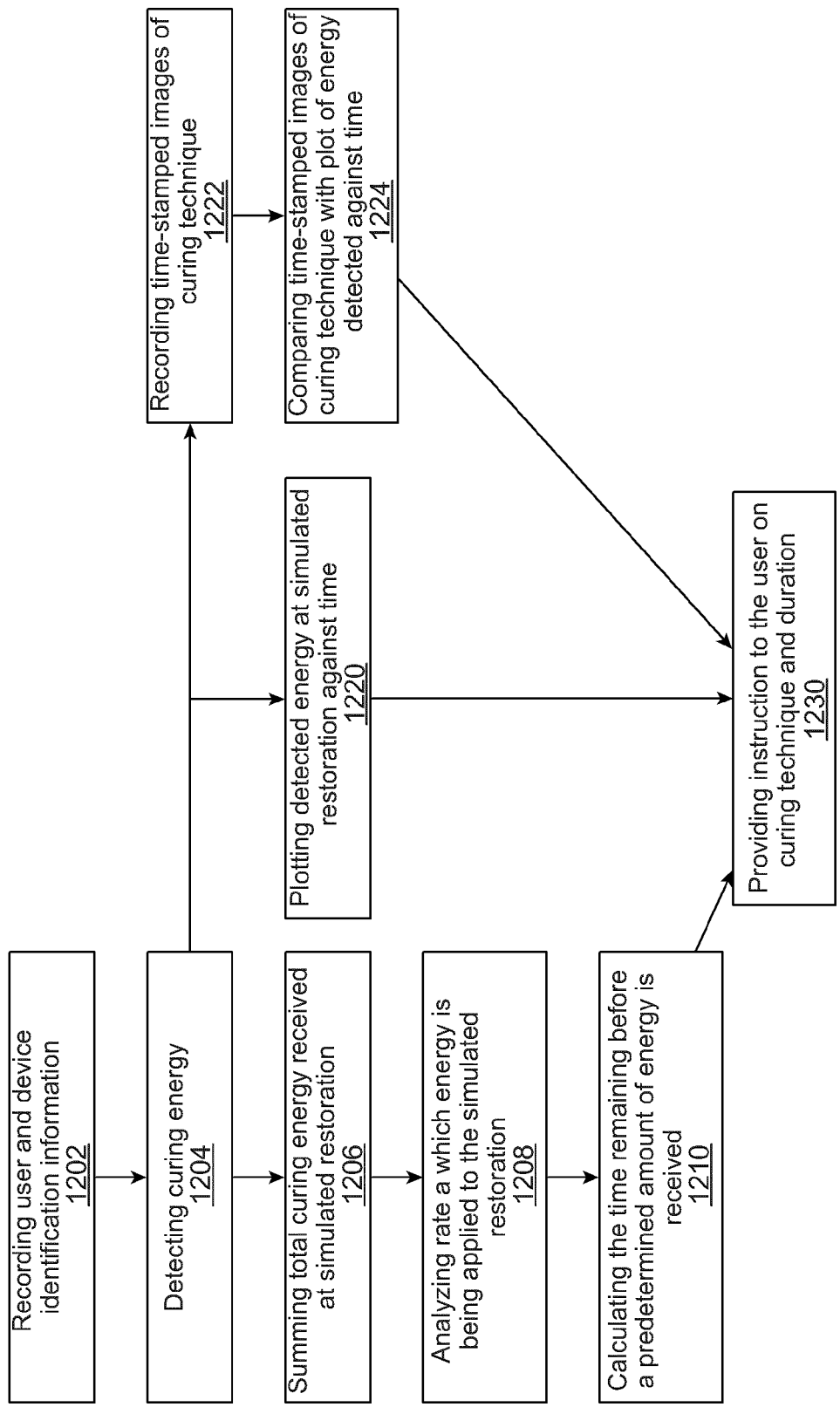
FIG. 12 illustrates exemplary method embodiments for providing feedback to an operator during a simulated resin restoration.

FIG. 12 illustrates exemplary methods of calculating a remaining duration for which to continue to apply curing energy to adequately cure the simulated restoration; of graphing energy received at the simulated restoration over time; and of comparing images or video of an operator's technique with optimal energy delivery. At 1202 operator and curing energy source identification information are entered into a user interface and are recorded in a database. The user identification and the device identification can be used to create profiles used in recording and organizing data associated with several trials having an operator or device in common. See, for example, FIGS. 8 and 10 illustrating examples of how such profile information can be useful in analysis across multiple trials by a common user or device.

Curing energy, e.g., electromagnetic radiation, is detected by the system's detector embedded within the simulated restoration at 1204 and the amount of energy received at the detector can be displayed in real-time 1206. Substantially simultaneously with the curing energy being detected by the detector, a system timer can be initialized and used to determine the rate at which curing energy is being applied to the simulated restoration 1208. Using the amount of energy received at the simulated restoration and the rate at which the energy is being applied, the system can calculate a time remaining before a predetermined amount of energy is received at the restoration 1210. The predetermined amount of energy can be a recommended amount of energy needed to cure a restoration based on manufacture's instructions.

The amount of energy detected by the detector can also be plotted against time 1220 and saved for later review. A camera can also record still pictures or videos of the operator's technique in delivering the curing energy to the simulated restoration 1222. The videos or still images are further associated with a timestamp that corresponds to the other graphs generated by the system. Using the timestamp, the graph of energy detected by time can be compared against the still or video images of the operator's curing technique 1224.

Each of the calculated time remaining to provide a sufficient cure, the graph of energy received by time, and the comparison of images of the operator's curing technique with the graph can further be used in providing instruction to the user on proper curing technique 1230.

In some embodiments, a temperature sensor is provided and can be used to evaluate curing technique and different energy sources. In such embodiments, the temperature sensor can be positioned in or on a tooth or the simulated oral tissues adjacent to the tooth to which the curing energy is being delivered. The temperature sensor can be connected to the processor, and in such embodiments the processor is configured to output the recorded temperature and/or temperature increase in both real-time and average temperature during curing. The data from the temperature sensor can also be reported to the database and can be displayed in user interfaces for comparison of recorded temperatures across different light sources or users. See for example Table 1, below.

TABLE 1

| Curing Light | Mode | Curing Time | Sensor | ° C. |
|---|---|---|---|---|
| Bluephase 20i (T) 2 × 5 s | turbo | 2 × 5 s | MARC | 3.6 |
| VALO (H) 3 × 4 s | high | 3 × 4 s | MARC | 3.6 |
| VALO (P) 2 × 3 s | plasma | 2 × 3 s | MARC | 3.5 |
| VALO (S) 1 × 20 s | standard | 1 × 20 s | MARC | 3.4 |
| Bluephase 20i (H) 1 × 15 s | high | 1 × 15 s | MARC | 3.0 |
| Elipar S10 (S) 1 × 10 s | standard | 1 × 10 s | MARC | 2.8 |
| VALO (H) 2 × 4 s | high | 2 × 4 s | MARC | 2.7 |
| DEMI (S) 1 × 10 s | standard | 1 × 10 s | MARC | 2.5 |
| Sapphire (S) 1 × 5 s | standard | 1 × 5 s | MARC | 2.4 |
| Bluephase 20i (T) 1 × 5 s | turbo | 1 × 5 s | MARC | 2.2 |

As illustrated in Table 1, several different curing lights were compared using different modes and applied for different curing times. A mannequin embodiment having a temperature sensor was used to record the change in temperature during application of the curing energy. As illustrated in Table 1, the Bluephase 20i (Turbo mode) operated once for 5 seconds in turbo mode resulted in the least change in temperature as detected by the temperature sensor. Correspondingly, this light, operated in similar conditions would be least likely to result in pulpal or gum damage during a curing operation.

In some embodiments, an intra-oral camera can be provided and is either mounted inside the mouth of the mannequin or it can be in a detached configuration. The camera can record video or still images of the curing energy source as an operator is manipulating it during a simulated restoration. The camera can further be connected to the processor, which can process the video or images and optionally insert a timestamp. The images or video can be used to evaluate the curing technique of the operator. Such evaluation can be enhanced using the timestamp to correlate the recorded technique with the light delivery data detected at the same time point.

Figure 17A:
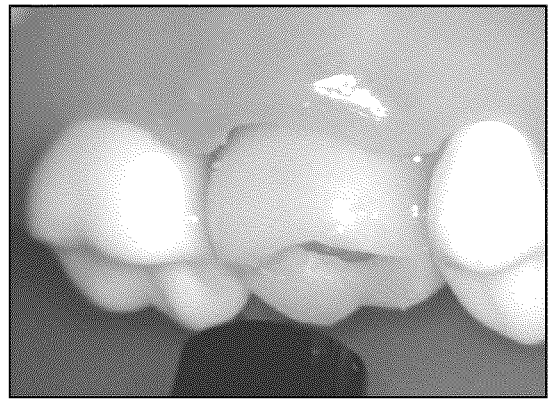
FIG. 17A is an image recorded by an intra-oral camera of a curing light positioned next to a tooth simulating a cavity condition.
Figure 17B:
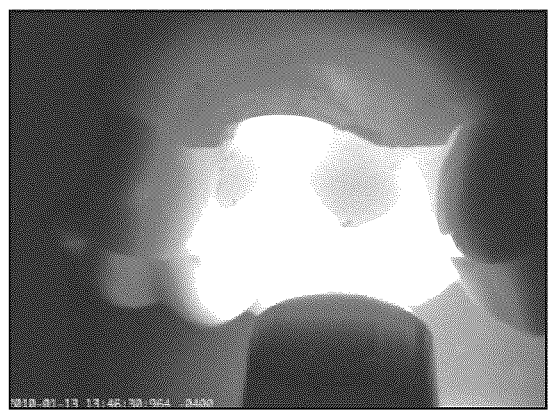
FIG. 17B is an image recorded by an intra-oral camera of a curing light delivering curing energy to a tooth simulating a cavity.

FIGS. 17A and 17B show images recorded by the intra-oral camera. In FIG. 17A, the curing-energy source is shown in position, but before operation. In FIG. 17B, the curing-energy source is shown delivering curing energy to the simulated restoration. A timestamp is also printed on the bottom of the image.

Figure 18:
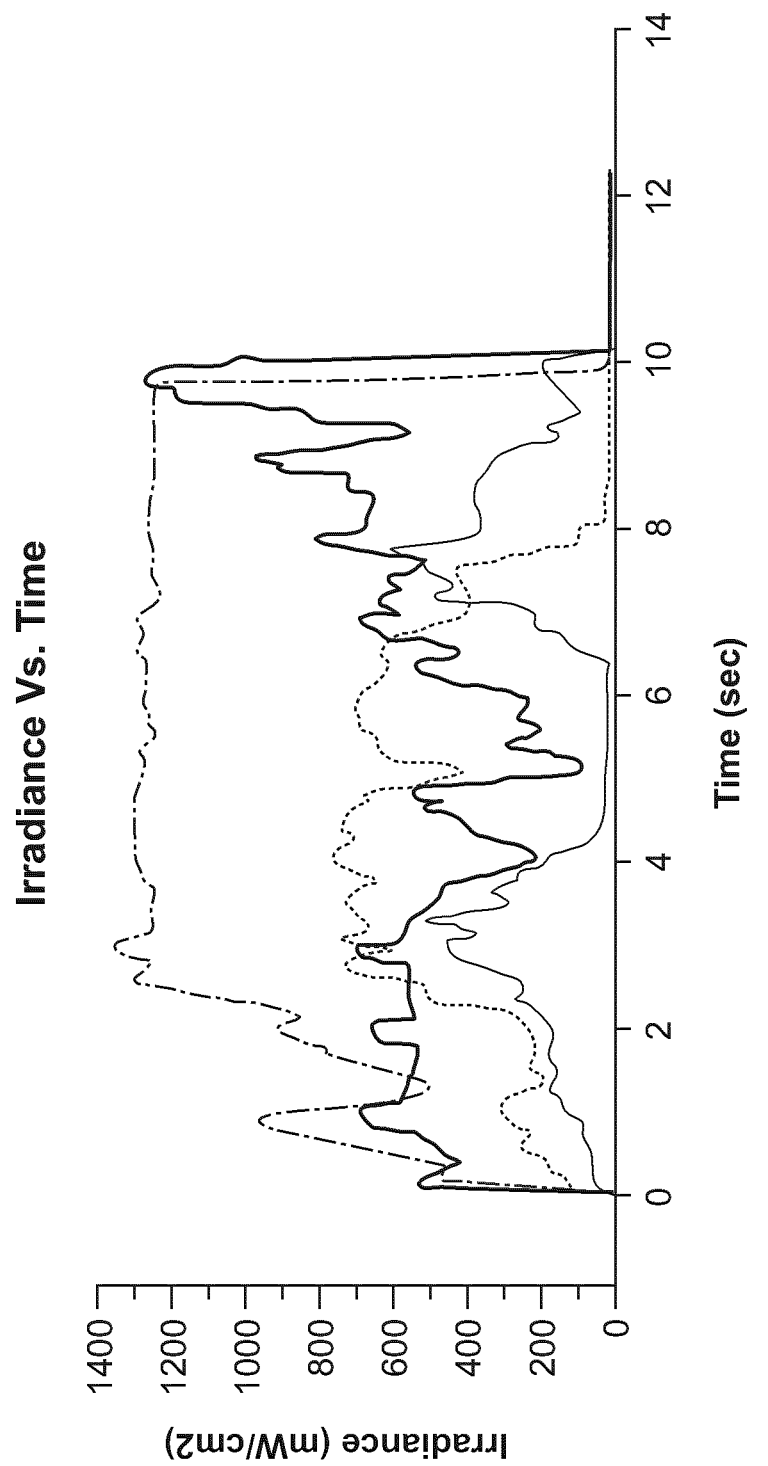
FIG. 18 is a graph of energy detected (irradiance) by time.

The amount of energy detected while the light in FIG. 17B is being operated can be plotted overtime as shown in FIG. 18. By comparing the timestamp in FIG. 17B with the graph in FIG. 18, an operator can further evaluate and learn from previous simulated restorations. When the energy detected is a higher value, at that time the operator has positioned the curing energy source in a more efficient position for delivering curing energy. An operator can compare their curing technique at that time point with their curing technique at a time point when the energy detected is a lower value to differentiate better and worse technique.

In sum, aspects of the system for real-time measurement of curing energy delivered to simulated dental restoration described herein provides a robust tool not only for providing real-time feedback to users about their ability to provide adequate curing energy to dental restoration, but also to develop user and curing energy source profiles stored both locally and remotely for comparison, training, and product development.

An experiment to illustrate the method for real-time measurement and optimization of curing energy delivered to a simulated dental restoration will now be described.

Most research studies test curing lights and resin curing in ideal laboratory settings with the end of the light guide at 90° and 0 mm from the specimen. From this research, most manufacturers recommended that their dental resins should receive between 12 to 24 J/cm². It has also been reported that a minimum of 24 J/cm² is necessary in order to obtain homogeneity of cure in 2 mm thick specimens. However, depending on the brand of resin composite the surface hardness may still benefit from increasing the radiant exposure to 36 J/cm².

It is reasonable to assume the amount of light received by a restoration under ideal laboratory settings with the light guide tip at 90° to the specimen and a distance of 0 mm would be quite different than in the intra-oral environment. Clinically, there are a number of challenges that face a clinician where the intra-oral environment is relatively small and dark. This can result in limited access and poor visualization. The intra-oral environment also has several hard to reach areas, such the distal aspect of maxillary molars, which makes proper angulation of the light guide difficult to achieve. Due to these less than ideal conditions, one can reasonably assume that some variability would exist in the amount of light energy that is received clinically by composite resin restorations.

When the composite resin receives an inadequate amount of energy, the resin will be inadequately polymerized. This is undesirable because the physical and chemical properties of the restoration are adversely affected. This may adversely affect the physical and chemical properties of the restoration, and decrease the biocompatibility of the restoration.

Materials and Methods

After obtaining appropriate Dalhousie University Ethics Committee approval, 20 dental student and dental assistants volunteers were asked to light cure a simulated Class I restoration in a mannequin head attached to a dental chair.

To determine the irradiance and energy that was delivered to a Class I restoration in an upper first second molar tooth #2.7, a 3.9 mm diameter cosine corrector detector (CC3-UV, Ocean Optics, Dunedin, Fla.) attached to spectroradiometer (USB 4000, Ocean Optics) detector was placed 2 mm from the occlusal surface and 4 mm from the cusp tip of a tooth that had been made out of Vit-l-escence (Ultradent, South Jordan, Utah) Shade A2 dental resin composite. The tooth was inserted into a dentoform that was placed in a NIS-SIM Simulation Head (Kilgore, Coldwater, Mich.) and attached to a dental chair in the Dental Clinic at Dalhousie University.

Prior to use, the curing light energy sources were calibrated using a NIST-traceable light source (LS-1-CAL, Ocean Optics).

The amount of curing light energy delivered by a conventional quartz-tungsten-halogen (QTH) light with a 10 mm standard light guide (Optilux 401, Kerr Corporation, Orange, Calif.) was determined in this simulated clinical setting. As recommended by the manufacturer of the resin composite the volunteers cured the simulated restoration using the Optilux 401 curing light for 20 seconds and the irradiance (mW/cm²) received by the Class I restoration was collected and analyzed at a later date.

The instructions given to each volunteer was to position the chair and mannequin head as they would for a patient and then to cure the Class I restoration in tooth #2.7 as they would for a patient. The volunteers were observed as they cured the simulated restoration. Any technique, which possibly contributed to a volunteer delivering a low amount of energy to the tooth was noted. It was observed that volunteers, who did not wear eye protection, did not look at the preparation, did not stabilize the curing light with their hand, and those who were not paying attention consistently delivered a low energy value.

Following these observations each volunteer was given coaching and taught how to optimize light curing a dental restoration. Specifically they were instructed to wear eye protection, look at the preparation, stabilize the light with their hand, and to pay attention. Therefore data was collected before and after proper curing light instruction. The before and after results were subjected to an analysis of variance followed by a paired Students t-test ($\alpha=0.05$).

The amount of curing energy required to adequately cure composite resin was calculated based on the amount of energy required to adequately cure 2 mm thick specimens of Filtek Supreme A2B by delivering different amounts of energy from 2 to 20 J/cm² from a QTH curing light to the specimens. To provide a clinically relevant reflective background surface the metal ring (2 mm thick with a 6 mm internal diameter) was placed on a mylar strip (Mylar, Du Pont Co., Wilmington, Del.) on a flat rectangular slab of resin composite (8.6×5.6 cm) and shade A2 (Vit-l-essence, Ultradent. Inc.). The Filtek Supreme A2B composite was packed into the ring and covered with another Mylar strip and a glass slide was pressed down over the specimen to produce a smooth flat surface. The composite was cured using different amounts of energy from 2 to 20 J/cm² from the QTH curing light. The cured samples were stored in air in the dark at room temperature for 24 hours to allow for post-curing. Samples were then placed on an automated hardness-testing machine (Model # HM 123, Mitutoyo Canada Inc. Mississauga, ON). The hardness tester was pre-programmed to measure 9 Knoop hardness values spread over the surface of the specimen in a matrix pattern, ensuring that at least a 1 mm buffer area was maintained around the specimen's edge to minimize any effect the mould may have on resin polymerization. The mean Knoop hardness (KNH) of the top and bottom surfaces of the 2 mm thick composite disks was measured. The critical amount of energy required for the bottom surface to reach 80% hardness of the top was calculated.

Results

Figure 13:
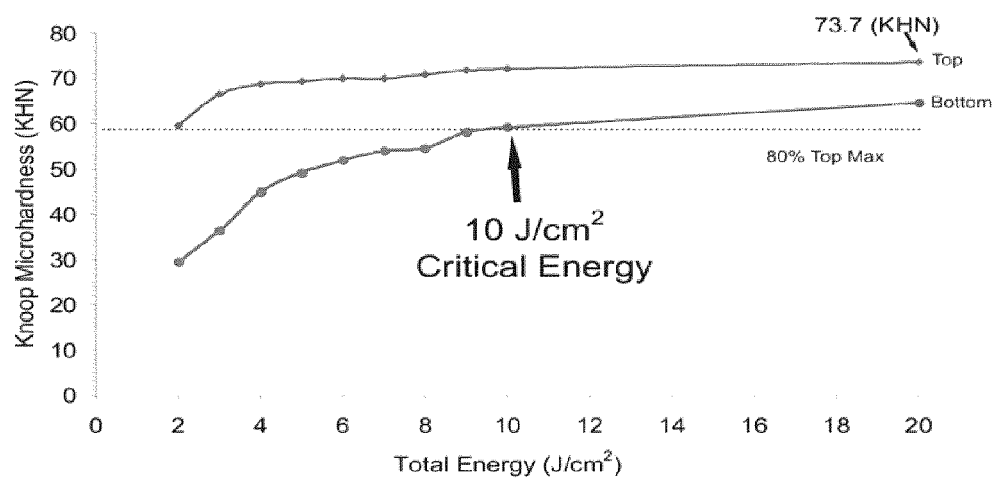
FIG. 13 is a graph illustrating the effect on the Knoop Hardness at the top and bottom of 2 mm thick specimens of Filtek Supreme A2B as a function of curing energy received.

The critical amount of energy required for the bottom surface of Filtek Supreme A2B composite to reach 80% hardness of the top was 10 J/cm² as shown in FIG. 13 and reported in Table 2. The Knoop Hardness (KHN) reported is the mean±S.D. of three repetitions with nine recording made on each surface (n=27 KHN recordings at each surface and at each energy level). At least 10 J/cm² was required for the bottom surface to reach 80% of the maximum hardness achieved at the top.

Table 2: Knoop Hardness measurements at the top and bottom of 2 mm thick specimens of Filtek Supreme A2B

TABLE 2

| Energy (J/cm²) | Mean Top KHN | S.D. | Mean Bottom KHN | S.D. |
|---|---|---|---|---|
| 2 | 59.7 | 4.6 | 29.5 | 5.2 |
| 3 | 66.5 | 3.5 | 36.5 | 8.2 |
| 4 | 68.7 | 2.4 | 45.0 | 7.5 |
| 5 | 69.3 | 3.0 | 49.3 | 8.7 |
| 6 | 70.0 | 2.4 | 51.9 | 8.7 |
| 7 | 70.0 | 3.8 | 54.1 | 6.6 |
| 8 | 70.9 | 2.0 | 54.6 | 6.4 |
| 9 | 71.7 | 1.8 | 58.2 | 4.2 |
| 10 | 72.1 | 2.3 | 59.2 | 6.1 |
| 20 | 73.7 | 2.6 | 64.7 | 5.7 |

Figure 14A:
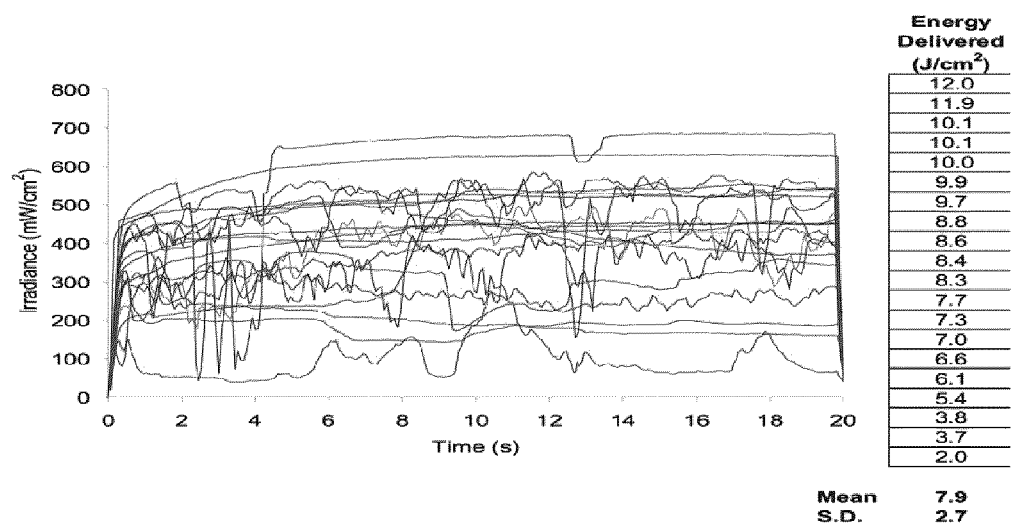
FIG. 14A is a graph illustrating the irradiance and energy delivered by participants during 20 seconds of light curing with Optilux 401 (a Quartz Tungsten Halogen light) light before receiving light curing instructions.
Figure 14B:
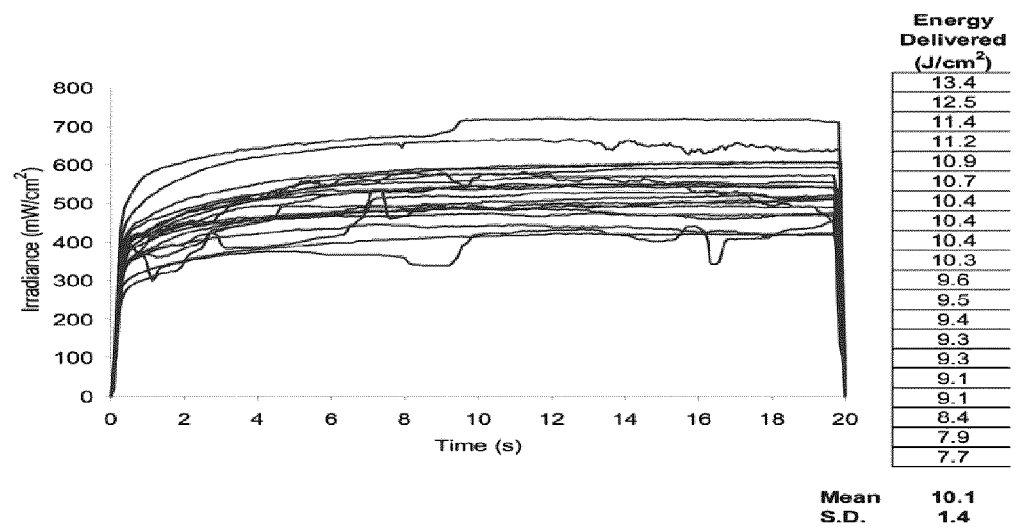
FIG. 14B is a graph illustrating the irradiance and energy delivered by participants during 20 seconds of light curing with Optilux 401 light after receiving light curing instruction.

Before proper curing light instruction, the amount of energy delivered by the 20 volunteers ranged from 2 to 12 J/cm$^2$; resulting in an average±S.D. of 7.87±2.69 J/cm$^2$, as shown in FIG. 14A. After receiving instruction, the amount of energy delivered by the 20 volunteers ranged from 7.8 to 13.4 J/cm$^2$; resulting in an average±S.D. of 10.05±1.42 J/cm$^2$, as shown in FIG. 14B. A paired Students t-test showed that instruction made a significant improvement (p=0.004). Table 3 summarizes the statistical tests on the data obtained.

TABLE 3

Statistical Analyses

ANOVA Table for J/cm2

| | DF | Sum of Squares | Mean Square | F-Value | P-Value | Lambda | Power |
|---|---|---|---|---|---|---|---|
| Group | 1 | 47.111 | 47.111 | 10.203 | .0028 | 10.203 | .893 |
| Residual | 38 | 175.461 | 4.617 | | | | |

Means Table for J/cm2
Effect: Group

| | Count | Mean | Std. Dev. | Std. Err. |
|---|---|---|---|---|
| After | 20 | 10.049 | 1.420 | .318 |
| Before | 20 | 7.878 | 2.687 | .601 |

Paired t-test
Hypothesized Difference = 0

| | Mean Diff. | DF | t-Value | P-Value |
|---|---|---|---|---|
| Before, After | −2.171 | 19 | −4.949 | <.0001 |

Figure 15A:
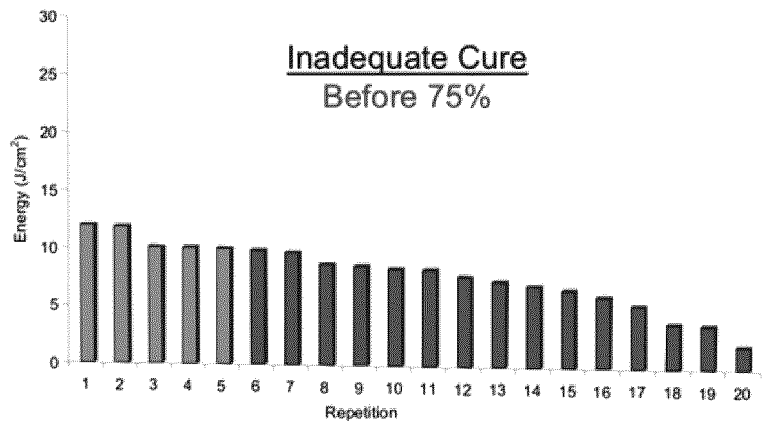
FIG. 15A is a graph illustrating the amount of energy delivered by participants before receiving light curing instructions.
Figure 15B:
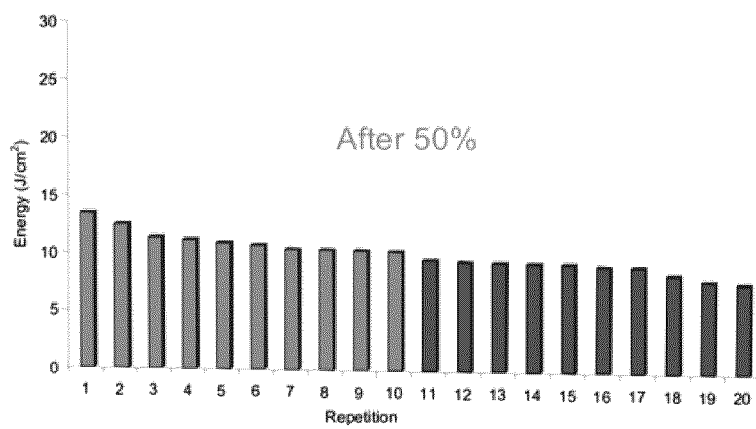
FIG. 15B is a graph illustrating the amount of energy delivered by participants after receiving light curing instructions.

From the results obtained, it was clear most volunteers did not deliver the critical amount of energy. Before curing light instruction 75% of volunteers did not deliver 10 J/cm$^2$ of energy, as shown in FIG. 15A. After curing light instruction, 50% of volunteers still did not deliver 10 J/cm$^2$ of energy using a 20 second cure, as shown in FIG. 15B.

Figure 16A:
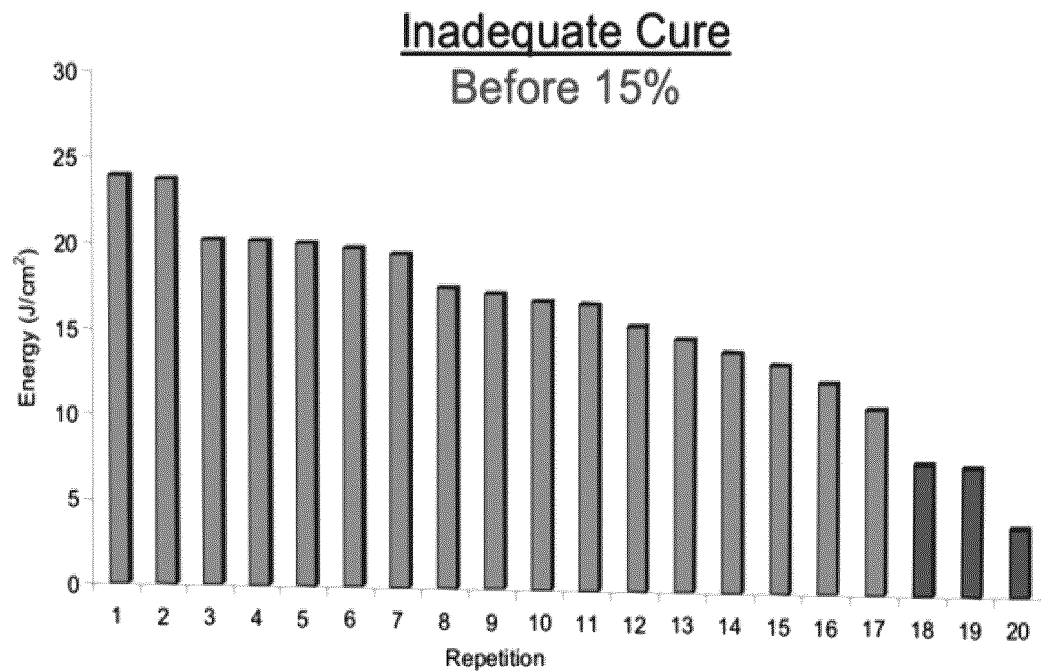
FIG. 16A is a graph illustrating the amount of energy delivered by participants during 40 second of light curing before receiving light curing instructions.
Figure 16B:
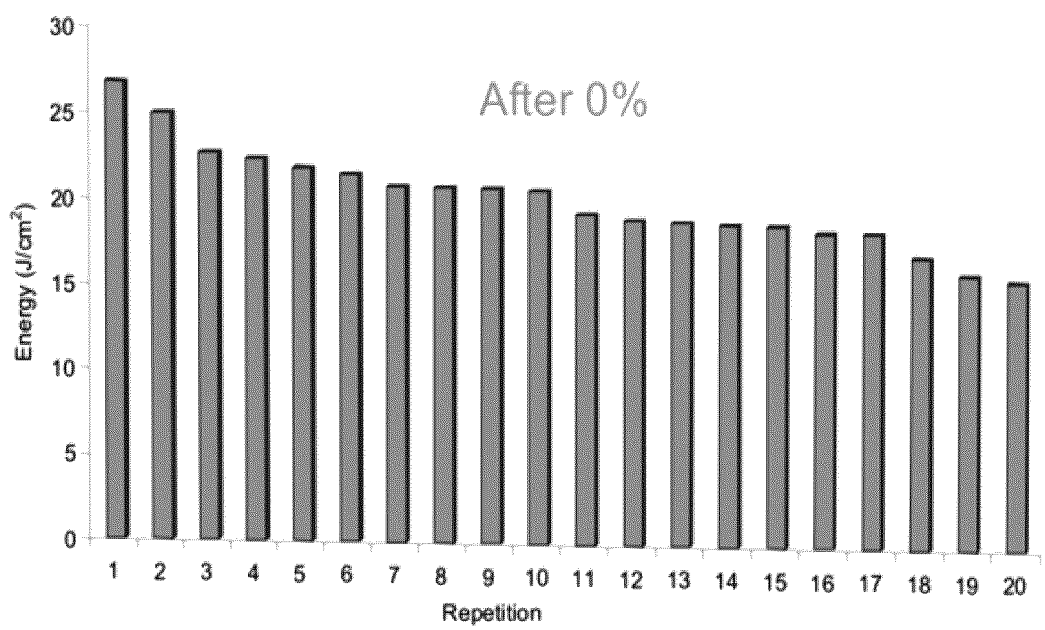
FIG. 16B is a graph illustrating the amount of energy delivered by participants during 40 seconds of light curing after receiving light curing instructions

FIG. 16A is graph illustrating the total amount of energy delivered by participants during 40 second of light curing before receiving light curing instructions showing that 15% did not deliver 10 J/cm$^2$ of energy using a 40 second cure, but as shown in FIG. 16B all users delivered 10 J/cm$^2$ of energy using a 40 second cure after instruction.

Discussion

In this simulated clinical investigation 20 volunteers cured a Class I restoration with a QTH curing light for 20 seconds and the energy (J/cm$^2$) received by the restoration was calculated from the product of the irradiance received by the tooth (mW/cm$^2$)×exposure time (seconds). This study transferred curing light research from a laboratory into a clinical setting with real life implications. The results showed that there was a large variability in the amount of light that was delivered to the tooth by the 20 volunteers. The majority of the volunteers did not deliver 10 J/cm$^2$ to the simulated restoration. The average energy±standard deviation (J/cm$^2$) received by a Class I restoration was 7.9±2.7 J/cm$^2$ before curing light instruction, which is less than the critical amount of energy required for the bottom of the composite to reach 80% of the hardness reached at the top.

This study indicated that many resin restorations may not be receiving an adequate amount of energy and may not be sufficiently polymerized. As described earlier, this may result in reduced physical properties, reduced bond strengths, increased wear and breakdown at the margins of the restoration, and decreased biocompatibility and increased DNA damage from the leachates. In vitro studies have shown that inadequately polymerized resin components can evoke either immunosuppression or immunostimulation on mitogen-driven proliferation of purified T-lymphocytes and spleen cells.

Proper curing light instruction made a significant improvement (p=0.004) and the manufacturers' minimum recommendations were just met, as the average energy±standard deviation delivered was 10.0±1.4 J/cm$^2$. All volunteers' improved the energy (J/cm$^2$) they delivered to the restoration after instruction (before=7.9 after=10.0 J/cm$^2$), and became more consistent (standard deviation before=2.7 after=1.4 J/cm$^2$). This underscored the significance of proper curing light technique to achieve the critical amount of energy. For instance, during a lengthy restorative procedure it is one of the last steps, which often gets the least attention and it is a common for clinicians to treat curing time as a break time. During the clinical investigation, it was noticed some volunteers had excellent curing light technique, while others had poor curing light technique. This affects the amount of energy delivered as the range was between 2.0 J/cm$^2$ (the lowest before instruction) to 13.4 J/cm$^2$ (the highest after light curing instruction). As a general observation, it was common for the volunteers to point the curing light on the tooth, press the ON button, and then look away from the bright blue light. During the 20 seconds, the curing light would drift farther and farther away. In the most extreme example, the curing light finished on a completely different tooth. Very few volunteers used eye protection that was provided. All volunteers made a significant improvement in curing light technique when four simple instructions i.e., to wear eye protection, to look at the preparation, to stabilize the light with their hand, and to pay attention were followed.

The curing instructions for Filtek Supreme Shade A2B recommend 20 seconds of light curing. However, based on the amount of energy delivered, it is recommended to use a 40 second cure time with the Optilux 401 (QTH) light to confidently ensure the critical amount of energy is being delivered in the mouth. All volunteers would have delivered the critical amount of energy if the curing cycle had been doubled to 40 seconds, as shown in FIGS. 16A and 16B. Extending duration of exposure to curing light energy may be implemented as a compensation technique for challenging clinical situations since the longer curing time results in more energy being delivered. It is noted that this recommendation may not apply to all areas of the mouth and depends on the ability to deliver adequate amount energy based on ease of reach.

Knoop micro-hardness has been shown to be one of the best methods for testing the hardness of composite resins and good correlation between degree of conversion and the Knoop microhardness has been previously reported. This study revealed that at least 10 J/cm$^2$ of energy must be received by Filtek Supreme Plus shade A2B composite resin from a QTH curing light in order for the bottom surface to reach 80% of the maximum hardness reached at the top. An important point to consider is the critical amount of energy required depends on the type of curing light a clinician uses. QTH lights are broad-spectrum lights while LED lights deliver a narrow spectrum and this will affect the critical amount of energy required to adequately cure composite resin. A comparison of the amount of light energy from a range of different curing lights delivering similar or different wavelengths that are used in dental restorations can be performed using the system described herein and the curing light with the optimum properties may be chosen for a particular dental restoration.

Thus, a method and system for measurement of curing energy and the wavelength of the electromagnetic radiation delivered during photocuring of simulated dental restorations, which can show the operator whether they are delivering sufficient curing energy to a restoration in real-time is provided.

Figure 19A:
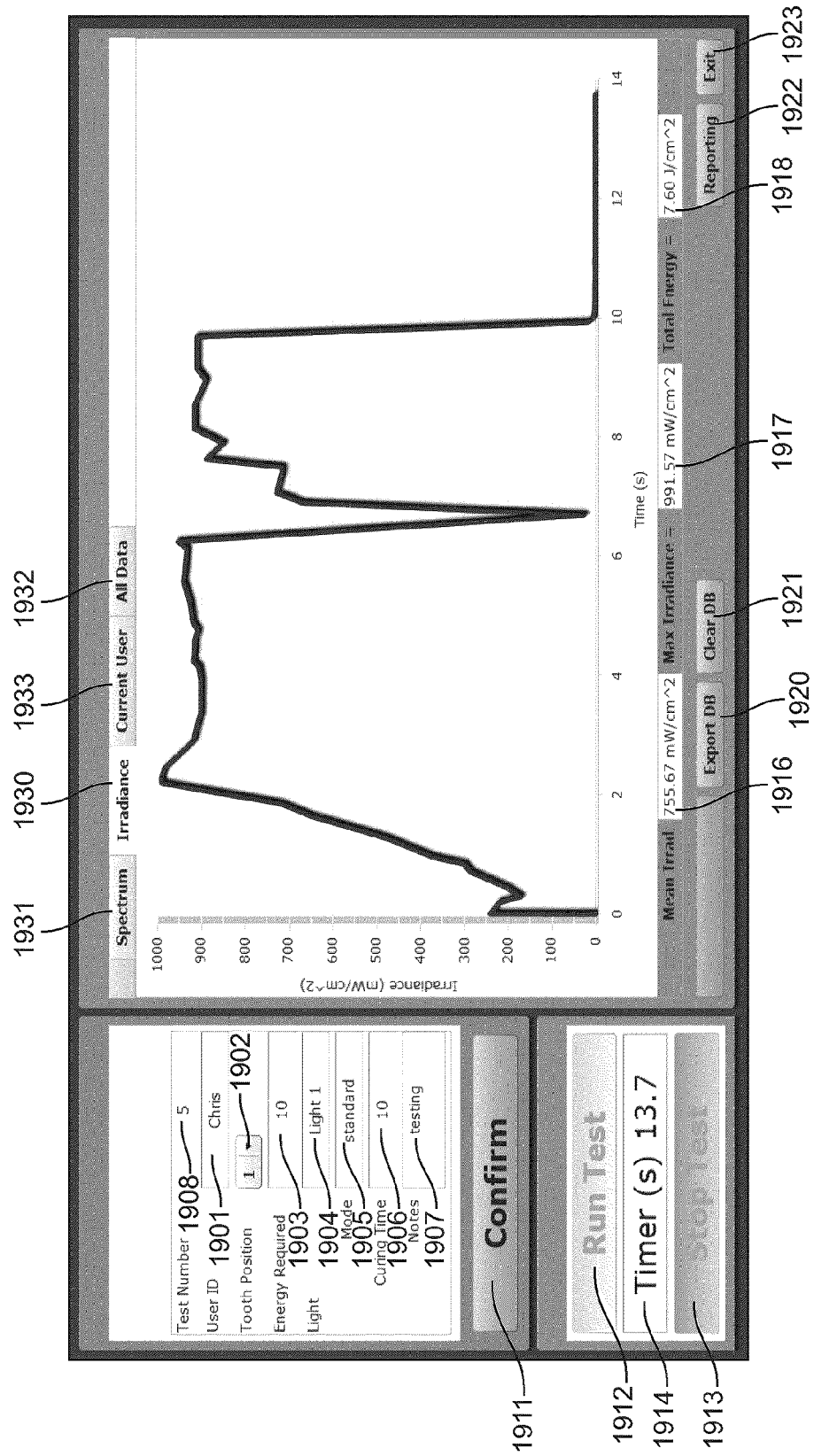
FIG. 19A is a user interface showing a graph of irradiance against time.
Figure 19B:
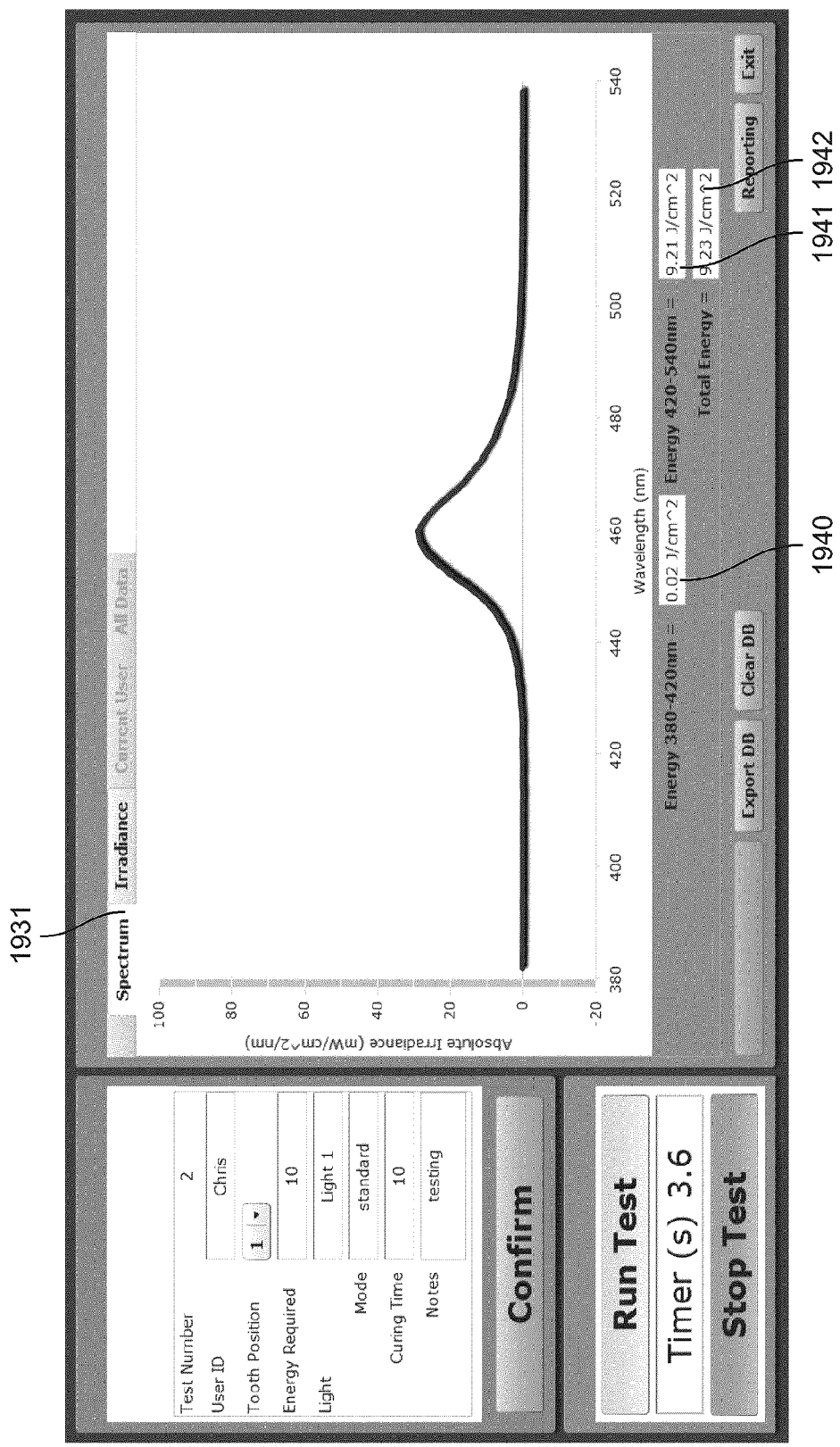
FIG. 19B is a user interface showing a graph of irradiance against wavelength.
Figure 19C:
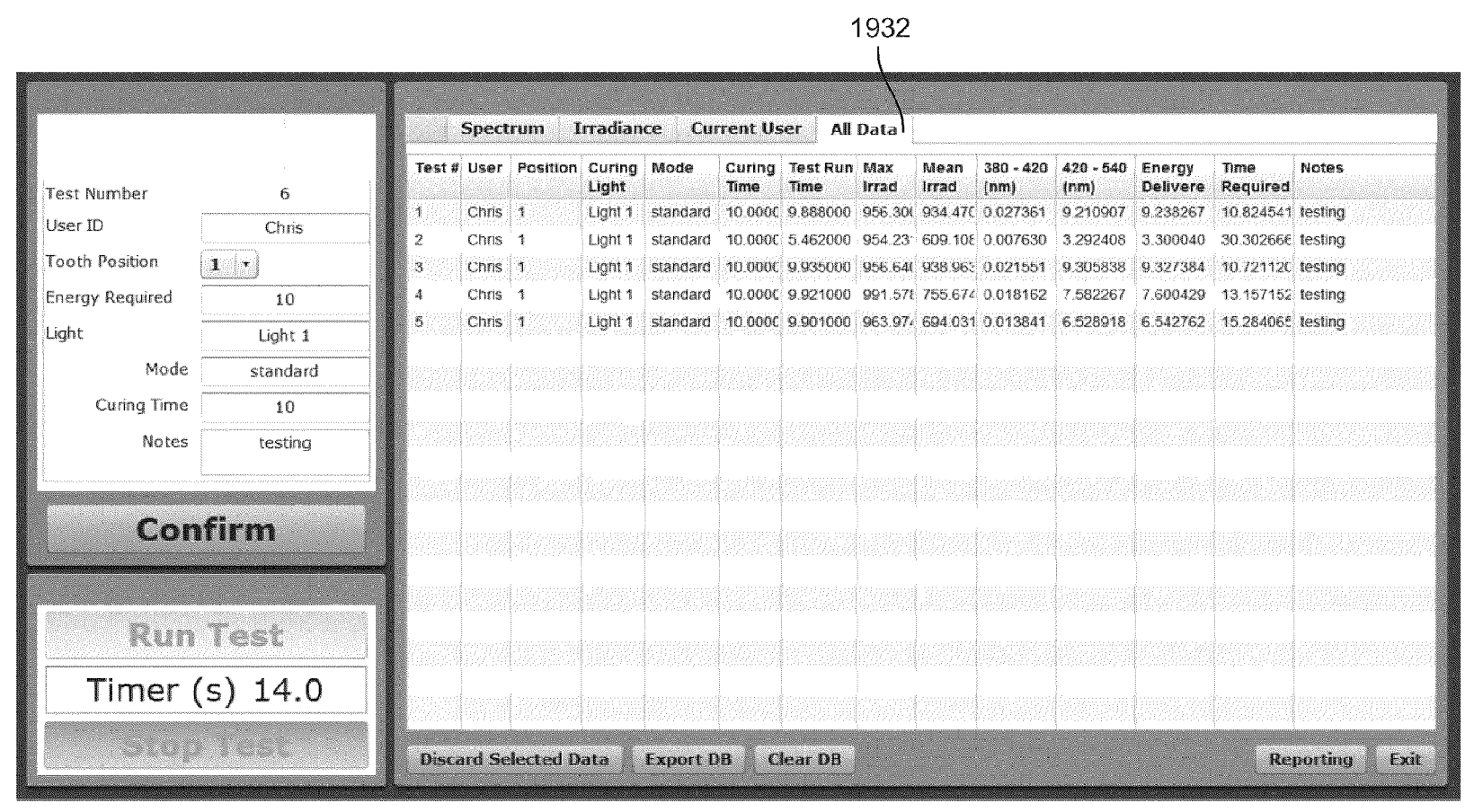

FIGS. 19A, 19B, 19C illustrate user interfaces that can be used with the system. FIG. 19A illustrates an interface which can accept user inputs such as user ID (1901), tooth position of the simulated restoration (1902), energy required (1903), light identification (1904), light curing mode (1905), curing time (1906), a notes field (1907), and test number identification (1908). In the interfaces displayed, user Chris ran test number 5 with light 1 operated in standard mode which resulted in the irradiance graph illustrated to the right. The user interface also has several other illustrated features such as a confirm button (1911) to confirm that the information is correct, a run test button (1912) to begin monitoring the simulated restoration, a stop test button (1913) to stop monitoring the simulated restoration, and a timer field (1914) illustrating the duration of the simulated restoration. The graph shows that in this trial run, the user apparently missed the target tooth at some point around 7 seconds resulting in a sharp drop off in irradiance and energy delivered. Further analysis is provided showing the mean irradiance (1916), the max irradiance (1917), and total energy delivered (1918). The interface further provides for exporting the data to a database (1920), clearing the data (1921), creating a report (1922) and exiting the interface (1923).

In addition, the interface has multiple possible views. In FIG. 19A the irradiance view is shown as illustrated by the irradiance tab (1930) being raised beyond the other tabs. FIG. 19B illustrates the spectrum view having the spectrum tab (1931) raised beyond the other tabs and FIG. 19C illustrates the all data tab having the all data tab (1932) raised beyond the other tabs. There is also a tab (1933) for the current user which can graph multiple tests from the same or multiple users.

FIG. 19B illustrates the spectrum view showing the absolute irradiance of light 1 being used in standard mode. In this instance, light 1 has a wavelength of approximately 460 nm. As illustrated, the spectrum view also shows additional data breakdowns of energy delivered by wavelength subset ranges of 380-420 nm (1940), 420-540 nm (1941) and total energy across the entire graphed wavelength range (1942).

FIG. 19C illustrates all data across all five of Chris' trial runs in a table.

In the preceding description, for purposes of explanation, numerous details are set forth in order to provide a thorough understanding of the embodiments of the invention. However, it will be apparent to one skilled in the art that these specific details are not required in order to practice the invention. In other instances, well-known electrical structures and circuits are shown in block diagram form in order not to obscure the invention. For example, specific details are not provided as to whether the embodiments of the invention described herein are implemented as a software routine, hardware circuit, firmware, or a combination thereof.

Aspects of the technology can be represented as a software product stored in a machine-readable medium (also referred to as a computer-readable medium, a processor-readable medium, or a computer usable medium having a computer-readable program code embodied therein). The machine-readable medium can be any suitable tangible medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the invention. Those of ordinary skill in the art will appreciate that other instructions and operations necessary to implement the described invention can also be stored on the machine-readable medium.

Software running from the machine-readable medium can interface with circuitry to perform the described tasks.

The above-described embodiments of the invention are intended to be examples only. Alterations, modifications and variations can be effected to the particular embodiments by those of skill in the art without departing from the scope of the invention, which is defined solely by the claims appended hereto.

What is claimed is:

1. A system for measurement of curing energy delivered during a simulated dental restoration from a source of curing energy, the system comprising:
   a detector positioned within a location of the simulated dental restoration in a tooth and configured to detect energy delivered by the source of curing energy to the location of the simulated dental restoration; and
   a display configured to display the detected amount of curing energy delivered to the location of the simulated dental restoration in substantially real-time, wherein the detector comprises a sensor connected to a spectroradiometer, and the curing energy is electromagnetic radiation.

2. The system of claim 1, further comprising:
   a dental mannequin including artificial cheeks, lips, a tongue, and a variable jaw opening, wherein the tooth is a simulated tooth.

3. The system of claim 2, further comprising:
   an intra-oral video camera configured to record video or still images of the simulated dental restoration and the source of curing energy.

4. The system of claim 3, wherein the video or still images include a timestamp.

5. The system of claim 2, wherein the simulated tooth is made from material having substantially similar optical properties of a natural tooth.

6. The system of claim 2, wherein the detector is positioned within the simulated tooth at a predetermined depth, thereby simulating a tooth cavity condition.

7. The system of claim 2, further comprising a curable material placed within the simulated tooth for exposing the curable material to the curing energy to simulate the dental restoration.

8. The system of claim 2, further comprising:
   a processor configured to determine a duration of time remaining for which the curing energy must be applied before the detector has received energy substantially equal to a predetermined amount of energy, the predetermined amount of energy being the amount of energy needed to be delivered to cure curable material at the location of the simulated dental restoration.

9. The system of claim 1, further comprising a temperature sensor positioned on or adjacent to the location of the simulated restoration.

10. A method for measurement of curing energy delivered during a simulated dental restorations, the method comprising:
   (a) providing a dental mannequin comprising artificial cheeks, lips, a tongue, at least one simulated tooth, a variable jaw opening, and a detector located within a simulated tooth-cavity condition in one of the at least one simulated tooth, wherein the detector comprises a sensor connected to a spectroradiometer;
   (b) delivering curing energy to the dental mannequin during a first simulated dental restoration;
   (c) measuring an amount of curing energy delivered to the detector, during the first simulated dental restoration;
   (d) displaying the measured amount of the curing energy delivered during the first simulated dental restoration in substantially real-time;
   (e) delivering curing energy to the dental mannequin during a second simulated dental restoration;
   (f) measuring an amount of curing energy delivered to the detector during the second simulated dental restoration;
   (g) displaying the measured amount of the curing energy delivered during the second simulated dental restoration in substantially real-time; and
   (h) comparing the measured amount of curing energy during the first and second simulated dental restorations,
   wherein the curing energy is electromagnetic radiation.

11. The method of claim 10, further comprising:
   measuring a change in temperature at a position adjacent to the tooth-cavity condition during the first or second simulated dental restoration and displaying the change in temperature.

12. The method of claim 10, further comprising:
   capturing video or still images of the first or second simulated dental restoration, the images having a timestamp.

13. The method of claim 12, further comprising:
   presenting the images at a given time point, represented by the timestamp, juxtaposed with values indicating the amount of curing energy delivered to the detector at the same time point.

14. The method of claim 13, wherein images are juxtaposed with a graph illustrating the amount of curing energy delivered to the detector by time, the timestamp of the images is correlated with the time represented in the graph.

15. The method of claim 10, wherein the curing energy delivered in steps (b) and (e) is delivered by the same light source.

16. The method of claim 15, wherein the curing energy delivered in steps (b) and (e) is delivered by the same person.

17. The method of claim 10, wherein the curing energy delivered in steps (b) and (e) is delivered by different light sources.

18. A device for measurement of curing energy delivered during a simulated dental restoration from a source of curing energy, the device comprising:
   a dental mannequin comprising artificial cheeks, lips, a tongue, at least one simulated tooth, a variable jaw opening, and a detector positioned within a location of the simulated dental restoration in one of the at least one simulated tooth;
   a display that displays the amount of curing energy detected by the detector during the simulated dental restoration in substantially real-time; and
   a processor configured to measure an amount of the curing energy delivered to the detector during the simulated dental restoration and display the measured amount of the curing energy in substantially real-time.

* * * * *